United States Patent [19]
Arnold et al.

[11] Patent Number: 4,922,915
[45] Date of Patent: May 8, 1990

[54] AUTOMATED IMAGE DETAIL LOCALIZATION METHOD

[75] Inventors: Ben A. Arnold, 4 Sandstone, Irvine, Calif. 92714; Alan H. Rowberg, Bellevue, Wash.

[73] Assignee: Ben A. Arnold, Irvine, Calif.

[21] Appl. No.: 406,836

[22] Filed: Sep. 13, 1989

Related U.S. Application Data

[63] Continuation of Ser. No. 126,631, Nov. 27, 1989, abandoned, which is a continuation-in-part of Ser. No. 48,004, May 11, 1987, abandoned, which is a continuation-in-part of Ser. No. 47,415, May 6, 1987, abandoned.

[51] Int. Cl.$^5$ ............................................. A61B 6/00
[52] U.S. Cl. ................................... 128/653 R; 382/6; 382/18; 378/18
[58] Field of Search ................. 128/653, 659; 378/18, 378/901; 364/413.13–413.14; 382/6, 18, 48, 61

[56] References Cited

U.S. PATENT DOCUMENTS

| | | | |
|---|---|---|---|
| 3,705,383 | 12/1972 | Frayer | 382/18 |
| 4,115,762 | 9/1978 | Akiyama et al. | 382/8 |
| 4,233,507 | 11/1980 | Volz . | |
| 4,475,122 | 10/1984 | Green | 382/8 |
| 4,593,406 | 6/1986 | Stone | 382/8 |
| 4,606,065 | 8/1986 | Beg et al. | 382/18 |

OTHER PUBLICATIONS

Heil, Jr. et al., "Quantitative Materials Evaluation and Inspection with the Imaging Analysing Computer", Proceedings of the Society of Photo-Optical Instrumentation Engineers, Feb. 1972, pp. 131–143.

K. P. Hermann et al., "Polyethylene-Based Water—Equivalent Phantom Material for X-Ray Dosimetry at Tube Voltages from 10 to 100 kV", Phys. Med. Biol., vol. 30, No. 11, 1985, pp. 1195–1200.

K. P. Hermann et al., "Muscle and Fat-Equivalent Polyethylene-Based Phantom Materials for X-Ray Dosimetry at Tube Voltages Below 100 kV", Phys. Med. Biol., vol. 31, No. 9, 1986, pp. 1041–1046.

Christopher E. Cann et al., "Precise Measurement of Vertebral Mineral Content Using Computed Tomography", Journal of Computer Assisted Tomography, vol. 4, No. 4, Aug. 1980, pp. 493–500.

Christopher E. Cann et al., "Low-Dose CT Scanning for Quantitative Spinal Mineral Analysis", Radiology, vol. 140, No. 3, Sep. 1981, pp. 813–815.

(List continued on next page.)

Primary Examiner—Ruth S. Smith
Attorney, Agent, or Firm—Knobbe, Martens, Olson & Bear

[57] ABSTRACT

An automated image detail localization system for digital image systems, such as CT, MRI, digital radiograph, includes a calibration phantom having plural reference samples of materials having known, fixed imaging properties. The phantom is positioned with respect to a patient and scanned simultaneously to produce an image that includes a cross-section of the patient and a cross-section of the phantom. The cross-sectional image of the phantom includes cross-sectional images of the reference samples. The system automatically finds the phantom and the centers of the reference sample images and then positions regions of interest (ROIs) within the reference sample images to define the portions of the images that are included in a step of averaging the intensities of the reference sample images. The system further automatically places an ROI of regular (e.g., elliptical) or irregular shape in a specific region of the image of the patient's anatomy, such as the trabecular bone region of the patient's spine. The system automatically performs a histogram analysis of the tissue within an ROI to exclude tissue components that are undesirable in the calculation of tissue density. By using the phantom in combination with the histogram analysis, component tissues that cannot be readily separated spatially can be isolated by density or signal intensity and thus quantified in an automated manner. Small or irregularly-shaped tissues, such as lung nodules, can be accurately quantified without requiring precise placement of an ROI in the tissue image.

25 Claims, 26 Drawing Sheets

OTHER PUBLICATIONS

Robert G. Zamenhof et al., "A Theoretical Sensitivity Evaluation of CT for the Measurement of Bone Mineral in Cortical and Vertebral Bone", *Journal of Computer Assisted Tomography*, Proceeding of CT Densitometry Workshop, vol. 3, No. 6, 1979, p. 852.

Technical Note, "Automatic Outlining Technique for EMI Scanner Pictures", *Med. & Biol. Eng. & Comput.*, 17, Sep. 1979, pp. 693–694.

R. E. Baldy et al., "A Fully-Automated Computer Assisted Method of CT Brain Scan Analysis for the Measurement of Cerebrospinal Fluid Spaces and Brain Absorption Density", *Neuroradiology*, vol. 28, 1986, pp. 109–117.

James M. Keller et al., "Automatic Outlining of Regions on CT Scans", *Journal of Computer Assisted Tomography*, vol. 5, No. 2, Apr. 1981, pp. 240–245.

W. A. Kalender et al., "Methodological Aspects of Bone Mineral Measurements by QCT: Minimizing Operator Influence on Reproducibility," Proceedings of the Sixth International Workshop on Bone and Soft Tissue Densitometry, Buxton, England, Sep. 22–25, 1987, p. 31.

P. F. Wankling et al., "Computer Recognition Applied to C.T. Scans for the Automation of the Procedure for Bone Mineral Measurement Allowing Consistent Measurement Without Operator Intervention," Proc. of the 6th Int'l Workshop on Bone and Soft Tissue Densitometry, Buxton, Engl., Sep. 22–25, '87, p. 32.

J. L. Grashuis et al., "Semi-Automatic Contour Detection in CT-Scans of the Lumbar Spine," Proceedings of the Sixth International Workshop on Bone and Soft Tissue Densitometry, Buxton, England, Sep. 22–25, 1987, p. 33, published in Calcified Tissue, vol. 44, No. 2, Feb. 1989, p. 147.

Willi A. Kalender et al., "Vertebral Bone Mineral Analysis: An Integrated Approach with CT," Radiology, vol. 164, No. 2, Aug. 1987, pp. 419–423.

Marketing materials from General Electric distributed in 1987 (four pages).

MEMORY ARRAY

| HU | COUNT |
|---|---|
| −1000 | 0 |
| −999 | 0 |
| −998 | 0 |
| 100 | 10 |
| 101 | 9 |
| 102 | 11 |
| 179 | 57 |
| 180 | 60 |
| 181 | 59 |
| 182 | 58 |
| 849 | 6 |
| 850 | 10 |
| 851 | 3 |
| 852 | 5 |
| 999 | 0 |
| 1000 | 0 |

ADDRESS BY HU — COUNTER DATA

SORTED HISTOGRAM TABLE

| HU | FREQUENCY |
|---|---|
| 180 | 60 |
| 179 | 59 |
| 181 | 58 |
| 182 | 58 |
| 177 | 58 |
| 178 | 57 |
| 185 | 53 |
| 172 | 50 |
| 175 | 49 |
| 200 | 44 |
| 215 | 44 |
| 170 | 44 |
| 150 | 30 |
| 225 | 30 |
| 100 | 10 |
| 850 | 10 |
| 99 | 9 |
| −1000 | 0 |

FIG. 29

AUTOMATED IMAGE DETAIL LOCALIZATION METHOD

RELATED APPLICATION

This application is a continuation of application Ser. No. 126,631 filed Nov. 27, 1989, now abandoned, is a continuation-in-part of U.S. patent application Ser. No. 048,004, filed May 11, 1987 for AUTOMATED DETAIL LOCALIZATION SYSTEM, now abandoned, which is also a continuation-in-part of U.S. patent application Ser. No. 047,415, filed on May 6, 1987, for AUTOMATED IMAGE DETAIL LOCALIZATION SYSTEM, now abandoned.

STATEMENT REGARDING MICROFICHE APPENDIX

A microfiche appendix is included as part of this specification.

NOTICE REGARDING COPYRIGHTED SUBJECT MATTER

A portion of the disclosure of this patent document contains material which is subject to copyright protection. The copyright owner has no objection to the facsimile reproduction by anyone of the patent document or the patent disclosure in its entirety, as it appears in the Patent and Trademark Office patent file or records, but otherwise reserves all copyright rights, whatsoever.

BACKGROUND OF THE INVENTION

1 Field of the Invention

The present invention is in the field of medical imaging including computerized tomography (CT), magnetic resonance imaging (MRI), general and/or digital radiography, or the like, and, more specifically, is related to the area of computer-assisted quantitative analysis of CT scans for bone mineral density and MRI for quantification of tissue with or without magnetic contrast agents, and digital radiography for bone density and other tissue measurements.

2 Description of the Prior Art

Computerized tomography (CT) is an imaging technique that uses an array of detectors to collect x-ray attenuation data from x-ray beams that pass through an object, such as a human body. The rotation of the x-ray beams and associated detectors about the object produces the equivalent of a "slice" through an area of interest, i.e., a planar cross-section of the human body. The x-ray attenuation data is collected as the x-ray beams are rotated and is input as digital data to a CT system computer. Specifically, computer algorithms programmed in the CT system computer process the digital attenuation data to reconstruct planar cross-sectional images of the "internal structures" through which the x-ray beams pass. The resulting reconstructed cross-sectional images are displayed on a video monitor, or the like. The reconstructed images inherently contain quantitative information about the x-ray attenuation of the internal structure of the object. Until recently, technical difficulties have prevented the full evaluation of the quantitative information.

Magnetic resonance imaging (MRI) is another technique that is developing wide acceptance in the medical imaging field. MRI relies on the principle that hydrogen atoms, when subjected to a magnetic field, become aligned. When a radio frequency signal is directed at the hydrogen atoms, the alignment of the nuclei of the atoms is changed. When the radio frequency signal is turned off, the nuclei realign in accordance with the magnetic field, and, at the same time transmit a small electric signal. The transmitted electric signals are received and converted into an image that is indicative of the hydrogen atoms that transmitted the signals. The strength of the image is analyzed to determine the densities of the hydrogen atoms and thus to determine the type of tissue corresponding to the image. Since MRI analyzes hydrogen content, it is particularly useful for analyzing soft tissues, such as the tissues of the brain. Although the invention is discussed below in connection with the use of CT systems to analyze bone mineral content, the invention is also applicable to MRI and other systems that provide images having image intensities that vary in accordance with the content of the tissue being scanned.

The CT technique was introduced by G. N. Hounsfield in 1972 to provide an enhanced, non-invasive way of imaging internal structures of an object, such as a human body. The technique is widely used for many diagnostic procedures throughout the human body, providing superior differentiation of "relative" attenuation of neighboring structures within the CT slice. The CT technique however has been ineffective for providing "absolute" attenuation measurements due to a variety of technical factors. This problem has more recently been overcome by scanning reference calibration samples simultaneously with the body of a patient, thus providing a standard for absolute calibration of tissue density, such as bone density for assessment of osteoporosis.

Osteoporosis is the most common disorder of the human skeletal system, affecting up to 32 percent of women and 17 percent of men, depending upon the age group under consideration. Basically, osteoporosis is a disease process in which the mineral content (i.e., calcium content) of a person's skeletal system is gradually reduced, leading to higher risks for fractures, particularly in the spine, hip and wrist. Osteoporosis is a major medical problem. It has been estimated that approximately 40,000 American women die per year from complications due to osteoporosis.

Osteoporosis, until recently, was considered to be undiagnosable prior to the onset of symptoms and untreatable, once it became symptomatic. Thus, it was frequently called the "silent disease." One of the many benefits obtained from the CT technique is its ability to isolate a volume of purely trabecular bone from surrounding hard cortical bone deep within the body, for example in a person's vertebrae. It has been found that the early stages of osteoporosis are characterized by early mineral loss in the trabecular bone of the spine. This is due primarily to the high metabolic turnover rate of trabecular bone that is about eight times higher than the turnover rate of cortical bone, the hard bone making up most of the skeletal system. Thus, a determination of the mineral content of the trabecular bone of the spine can be used for early detection of osteoporosis and can also be used to assess the effectiveness of therapies for prevention or reduction of further loss of mineral content in a person's bones.

Briefly, the CT technique is used to provide an image of a cross-section of a person's vertebrae, typically in the lumbar spine. The cross-section includes both the cortical (hard) bone of the vertebrae and the inner, more porous, trabecular bone. In addition, the cross-section includes various soft tissues of the surrounding body. As is well-known in the CT art, the intensity in a particular region of the CT image is directly related to the x-ray attenuation of that region of the internal structure of the body that corresponds to the same region in the image. As is well known in the art, the image comprises a two-dimensional display of pixels or voxels representing the attenuation properties of the internal structures. Each of the pixels has an intensity that corresponds to the attenuation of the x-rays by the corresponding region of the body structure. Typically, the intensity range, represented by attenuation of a portion of the image is measured in Hounsfield units (HU's). For example, the image produced as a result of the attenuation of x-rays by pure water has been assigned by convention to 0 HU; the image of air has been assigned −1000 HU; the image of hard cortical bone may vary up to the maximum range of +1000 HU. Thus, essentially any naturally occurring portion of the human body will attenuate the x-rays such that the resulting CT image will have an intensity representing an attenuation within the range of ±1000 HU. For example, the attenuation caused by dense bone may produce approximately 600-800 HU, while the attenuation caused by muscle, soft tissue and fat may vary in the range of +50 to −150 HU. Trabecular bone may vary widely, having an attenuation in the range of 50 to +300 HU, wherein an attenuation of 50 is representative of advanced osteoporosis and +300, or more, is exemplary of high trabecular bone density such as may be found in male athletes. Thus, a CT scan of a person's vertebrae can be used to isolate and measure the attenuation of the x-rays in the trabecular bone such that the mineral content of the trabecular bone can be determined, and thus the "health" of the patient's bones can thereby be determined.

It has been found however that the attenuation images produced in a CT apparatus vary significantly in response to a number of technical factors of the apparatus as well as the magnitude of errors caused by beam hardening and scattered radiation within the human body. For example, the effective energy of the x-ray beams and therefore beam hardening is different between different CT machines and dependent upon the x-ray tube and filtration. Thus, the image produced by one machine may visually appear similar to the image of the same patient produced on a different machine; however, the two images may produce significantly different "absolute" quantitative attenuation values. Furthermore, the x-ray tube of a CT apparatus is subject to changes with aging and with respect to the voltage applied to the x-ray source which may have long term and short term fluctuations with respect to time. In addition, scattered radiation varies with patient size and muscle/fat ratio, and varies with detector and collimator designs. Thus, an image taken with the same machine at different times or on different machines may vary irrespective of the variations in the internal structure of the patient's body. Thus, simple extraction of the pixel intensity from the image is not sufficient to provide reliable quantitative information regarding the mineral content of the trabecular bone.

The foregoing problem was recognized a number of years ago, and a reference standard was developed to quantitatively calibrate the image produced by the CT technique. The reference standard (referred to herein as a "calibration phantom") is disclosed in U.S. Pat. No. 4,233,507 to Donald J. Volz, which is incorporated herein by reference. Basically, the original calibration phantom includes a plurality of reference samples (for example, five), each of which comprises a material having known, fixed x-ray attenuation characteristics. For example, the reference samples may be liquid-filled containers, or cavities, located in a surrounding support structure. The liquids may be solutions of dipotassium hydrogen phosphate ($K_2HPO_4$), or, alternatively, may be solid plastic support material with homogeneously mixed calcium carbonate ($CaCO_3$), or calcium hydroxyapatite ($Ca_5(PO_4)_3(OH)$) powders, or the like. The samples are longitudinally disposed with respect to the patient and x-ray table, and are scanned simultaneously with the patient such that any slice through the patient also includes the cross-sectional images of the reference samples. The concentrations of the reference samples are selected to provide x-ray attenuations that simulate the attenuations of human bone or, alternatively, other human tissues. For example, in one exemplary embodiment of a calibration phantom having five reference samples, one of the reference samples comprises a solid having an approximate attenuation of −100 HU similar to fat; a second reference sample may comprise a solution having an a known fixed concentration of 0 mg/cc of $K_2HPO_4$ in pure water; a third reference solution may comprise a solution having a concentration of 50 mg/cc of $K_2HPO_4$ in pure water; a fourth reference sample may comprise a solution having a concentration of 150 mg/cc of $K_2HPO_4$ in pure water; and the fifth reference sample may comprise a solution having a concentration of 200 mg/cc of $K_2HPO_4$ in pure water. Thus, the first mentioned reference sample may simulate human body fat, and the other four reference samples may represent bone densities. An exemplary calibration phantom may also include a pair of metallic rods having an attenuation of 300-800 HU that can be used in some systems to locate the aforementioned cavities. An improved version of such a calibration phantom is described in copending U.S. patent application Ser. No. 015,047, filed on Feb. 17, 1987, entitled CALIBRATION PHANTOM FOR COMPUTER TOMOGRAPHY SYSTEM. The copending application is assigned to the assignee of this application, and is incorporated herein by reference.

In an exemplary prior art system, the calibration phantom is used to provide a reference by which the attenuation of the x-rays by the internal structures of the human body can be determined. Since the attenuations of the reference sample materials in each of the cavities is precisely known, the pixel intensities recorded in the images produced by x-ray attenuation in the reference samples and in the body structures, such as bone, can be recorded and compared to the known concentrations of the reference samples. A calibration relationship (i.e., a calibration factor) can then be calculated based upon the known concentrations of the calibration reference samples and the measured intensities of the images of the calibration reference samples. The calculated calibration relationship can then be applied to the measured intensities of the images of the internal structures of the body (e.g., the trabecular bone) and the absolute attenuation of each of the structures can then be determined and referenced to the standard of the calibration phantom in mg/cc of $K_2HPO_4$ bone density equivalence. Thus, the calibration phantom provides a way of determining the precise attenuation caused by a body structure irrespective of any deviations or fluctuations in the CT apparatus or due to biological variations from patient to patient or in the same patient on repeat scans.

In early uses of the calibration phantom, the measured image intensities were acquired by manual techniques. The operator of the CT system was required to define a region of interest (ROI) on the video display of the image of the calibration phantom. The region of interest ideally encompasses a substantial portion of the pixels that represent the image of one of the aforementioned reference samples. Each of the pixels within the region of interest has an intensity corresponding to the attenuation of the calibration material of the reference sample. Thus, the CT system computer can evaluate the intensity of the pixels and calculate the average intensity of the pixels within the region of interest. The measured intensity is then related to the known concentration of the reference sample by using linear regression analysis. All measured intensities are therefore related back to known, fixed standards of bone equivalence density. See, for example, Christopher E. Cann, et al., "Precise Measurement of Vertebral Mineral Content Using Computed Tomography,"*Journal of Computer Assisted Tomography,* Vol. 4, No. 4, August 1980, pp. 493–500; and Christopher E. Cann, "Low-Dose CT Scanning for Quantitative Spinal Mineral Analysis," *RADIOLOGY.* Vol. 140, No. 3, September 1981, pp. 813–815; both of which are incorporated herein by reference.

Typically, the region of interest (ROI) may be an approximately circular region of the video image that is graphically displayed by a bright outline on the video monitor. The ROI is adjusted for size and is positioned in the image of the reference sample by manually moving the ROI outline until it is positioned wholly within the reference sample image. The ROI outline can be moved by cursor control from a keyboard, manipulating a mouse or joystick, by manipulating a light pen, by entering coordinates from the keyboard, or other known manual procedures. Such manual procedures have been found to be very laborious and time consuming. The manual procedures are also subject to error caused by misplacement of the ROI such that it is not wholly within the portion of the image representing the reference sample. When this occurs, some of the pixels within the ROI may represent portions of the calibration phantom having a different attenuation than the attenuation of the calibration material comprising the reference sample. Thus, the measured intensities will not be correctly representative of the known concentrations of the reference samples, resulting in incorrect determinations of the equivalent densities of the various body structures. These problems are further aggravated because the operator must position an ROI for each of the plurality of calibration reference samples on multiple image slices for each patient, thus increasing the probability that one or more of the measurements will be incorrect. A similar problem occurs when the operator is positioning the ROI in the portion of the image representing the trabecular bone in the spine of the patient or other tissue areas to be quantized. It is important that the ROI encompass a substantial portion of the trabecular bone so that the averaged attenuation will more nearly represent the bone or tissue density. At the same time, it is important that the ROI not encompass the more dense cortical bone, as the attenuation of the cortical bone will distort the measurements of attenuation of the trabecular bone. Furthermore, since one of the primary purposes of the measurements is to monitor the mineral content of the trabecular bone over extended periods of time, it is important that the measurements be reproducible and less subject to changes or errors caused by variable manual procedures and human error. Thus, a need exists for a system for automating the positioning of the ROI's on a CT image.

SUMMARY OF THE INVENTION

One aspect of the present invention is an improved system for locating a region in an image generated by a computerized patient scanning system, such as a computerized tomography (CT) system. The present invention includes a calibrated phantom having a plurality of reference samples or cavities located therein and comprising materials that have known, predetermined x-ray attenuation characteristics. The calibration phantom is positioned proximate to the body of the patient, and is scanned as the patient is scanned so that an image is produced that includes a cross-section of the internal structure of the patient's body and that also includes a cross-section of the calibration phantom. The image includes a plurality of image pixels that are digital representations of the attenuation of the x-rays generated by the CT system. One aspect of the present invention is a method that includes the steps of scanning the pixels of the image and detecting the region of the image corresponding to the reference samples of the calibration phantom. The method accurately locates the centers of the reference sample images and positions regions of interest (ROI's) totally and reproducibly within the reference sample images so that the intensities of the pixels representing the reference sample images are accurately and precisely determinable.

In preferred embodiments of this aspect of the invention, the method includes the step of setting a pixel intensity search range that corresponds to the expected range of pixel intensities for one of the reference sample images. The method further includes the step of sequentially scanning the pixels in the image and evaluating the intensity of each pixel scanned until a pixel is detected that has an intensity within the intensity search range. The method further includes the steps of evaluating the intensity of pixels adjacent to the detected pixel and analyzing the adjacent pixels having intensities within the search range to determine whether each of the detected pixel is part of a reference sample image of known geometrical shape. If a sufficient number of adjacent pixels have intensities within the search range, then the method includes the steps of searching for the horizontal center of the reference sample image and searching for the vertical center of the reference sample image. Thereafter, the method includes the step of positioning a region of interest within the reference sample image with the center of the region of interest corresponding to the center of the reference image.

A further aspect of the present invention is a method for locating a region of interest within the image of the trabecular bone of a patient. The method includes the step of positioning a large region of interest in the image to encompass a substantial portion of the vertebral body including images of both the trabecular bone and the cortical bone. The method further includes the step of generating a boundary for a reduced region of interest within the region of purely trabecular bone and contained within the cortical bone rim. The image is first searched by detecting pixels along the boundary of the trabecular bone region of the image, and then defining a region of interest having a boundary within the boundary of the detected pixels. In one preferred embodiment, the region of interest is an ellipse having vertices defined by three pixels that are proximate to and within the boundary of the image of the cortical bone rim.

Another aspect of the present invention is an algorithm that searches for a region of the image, for example, the trabecular bone, by starting at a known location in the image of the phantom and analyzing the pixels in a predetermined direction from the known location.

Another aspect of the present invention is a method of analyzing image pixels in a non-homogeneous region or in an irregularly-shaped region by performing a histogram analysis of the image pixels in a region of interest. The histogram analysis results in a weighted average of image pixels having the most frequently occurring pixel intensities. This weighted average is correlated with a scale factor for the pixel intensities to calculate the average density of the tissue corresponding to the image pixels in the region of interest.

BRIEF DESCRIPTION OF THE DRAWINGS

FIG. 28 illustrates an exemplary memory array of the frequencies of occurrence of each Hounsfield units arranged in order of the Hounsfield units.

FIG. 29 illustrates a sorted memory array or table wherein the array is sorted in descending order of frequencies of occurrence.

DETAILED DESCRIPTION OF THE PREFERRED EMBODIMENT

Figure 1:
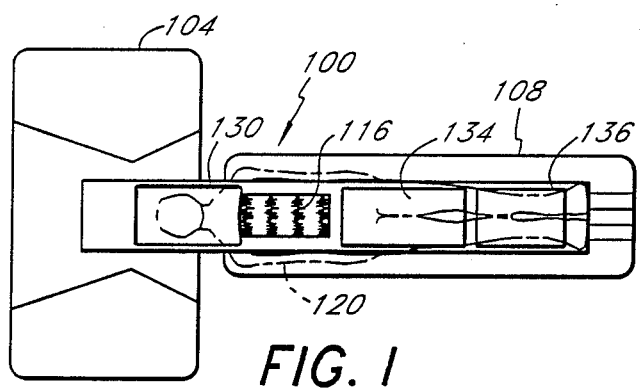
FIG. 1 is an plan view of an exemplary CT scanning system that includes a CT table for supporting a patient, a calibration phantom that is positioned under the spine of the patient, and a moveable gantry that supports an x-ray source and detectors.

FIG. 1 is an overhead view of an exemplary CT scanning system 100 for performing bone mineral analysis. The system includes a gantry 104 and a movable table 108. The movable table 108 preferably includes a location on its upper surface where a calibration phantom 116 is positioned. A patient 120 (shown in outline only) is positioned on the upper surface of the table 108 so that a portion of the patient's spine is positioned directly above the calibration phantom 116. The upper surface of the table 108 advantageously supports a series of cushions 130, 134, 136 that support the patient'head, hips and legs, respectively, to position the patient so that spine is properly located for the scanning procedure.

The CT scanning system also includes a CT system computer (not shown) that is included as part of the system. The CT system computer controls the operation of the system and receives and analyzes the data generated by each scan of the patient. Exemplary CT scanning systems that include CT system computers are available from General Electric Company, Siemens Medical Systems, Inc., Philips Medical Systems, Inc., Toshiba, and Picker Corporation. For example, General Electric Company of Milwaukee, Wis., sells models GE 8800, GE 9000, GE 9600 and GE 9800 that may be operated in accordance with the present invention to be described below.

Figure 2:
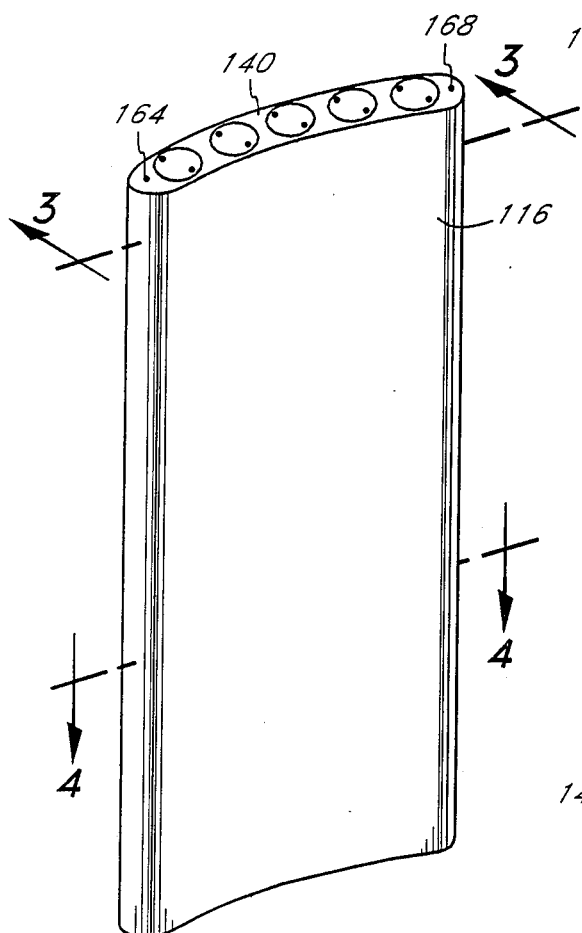
FIG. 2 is a perspective illustration of an exemplary calibration phantom.
Figure 3:
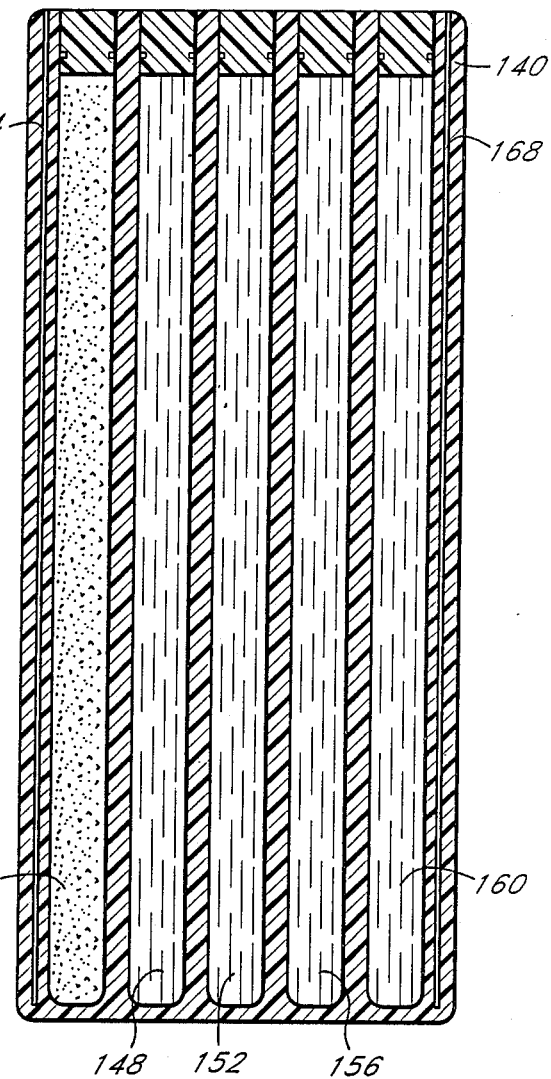
FIG. 3 is a cross-sectional view of the calibration phantom taken along the lines 3—3 in FIG. 2, showing the cavities filled with calibration reference material.
Figure 4:
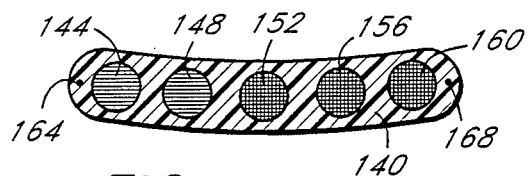
FIG. 4 is a cross-sectional view of the calibration phantom taken along the lines 4—4 in FIG. 2, showing the positions of the calibration reference samples within the phantom.
Figure 5:
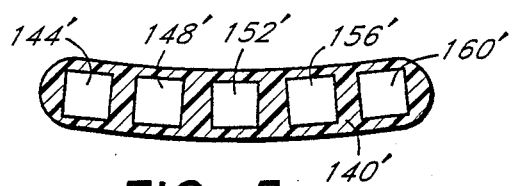
FIG. 5 is a cross-sectional view of an alternative embodiment of the calibration phantom illustrating an alternative geometrical cross-sectional configuration for the reference samples.

An exemplary calibration phantom 116 is illustrated in FIGS. 2, 3 and 4. As shown, the calibration phantom 116 may comprise an elongated, slightly arcuate or crescent-shaped base 140 that is advantageously molded as a single member with first, second, third, fourth and fifth elongated cavities 144, 148, 152, 156, 160 formed therein in side-by-side relationship. In addition, first and second elongated, small diameter metallic localization rods 164 and 168 may also be formed in the base 140. The metallic rods 164 and 168 are used in one aspect of the present invention for locating the cavities 144, 148, 152, 156, 160 on the video image produced by the system. As illustrated in FIG. 4, the cavities 144, 148, 152, 156, 160 advantageously have a circular cross-section. In the alternative, the cavities 144, 148, 152, 156, 160 can have a different geometric cross-section, such as a square cross-section, as illustrated by cavities 144', 148,, 152', 156', 160' in a body 140' in FIG. 5. It should be understood that the cavities 144, 148, 152, 156, 160 and the metallic rods 164 and 168, if present, are positioned in substantially parallel relationship with respect to each other. Furthermore, the cavities 144, 148, 152, 156, 160 and the rods 164 and 168 are spaced apart by precise distances so that once the position of the centers of any two of the cavities or rods is known, the positions of the remaining cavities can be accurately determined.

As described in U.S. Pat. No. 4,233,507 to Volz, the reference samples in the cavities 144, 148, 152, 156, 160 are comprised of materials having known attenuation characteristics. Each of the reference samples provides a predetermined x-ray attenuation characteristic that is similar to the x-ray attenuation characteristic of a portion of a human body. The five cavities 144, 148, 152, 156, 160 are typically filled with materials having different attenuation characteristics so that the reference samples provide a range of attenuation characteristics. For example, in an exemplary calibration phantom 116, the second cavity 148 is advantageously filled with pure distilled water; the third cavity 152 is advantageously filled with a solution of dipotassium hydrogen phosphate ($K_2HPO_4$) having a concentration of 50 milligrams of $K_2HPO_4$ per cubic centimeter of distilled water; the fourth cavity 156 is advantageously filled with a $K_2HPO_4$ concentration of 100 mg/cc; and the fifth cavity 160 is advantageously filled with a $K_2HPO_4$ concentration of 200 mg/cc. In exemplary embodiments, the first cavity 144 of the calibration phantom 116 typically is filled with a calibrated sample that has x-ray attenuation characteristics that are equivalent to human body fat. Although described herein with respect to the calibration phantom 116 having the cavities filled with solutions, it should be understood that the reference samples can also advantageously be solid portions of a calibration phantom having selected x-ray attenuation characteristics provided by calcium carbonate powders, or the like.

Figure 6:
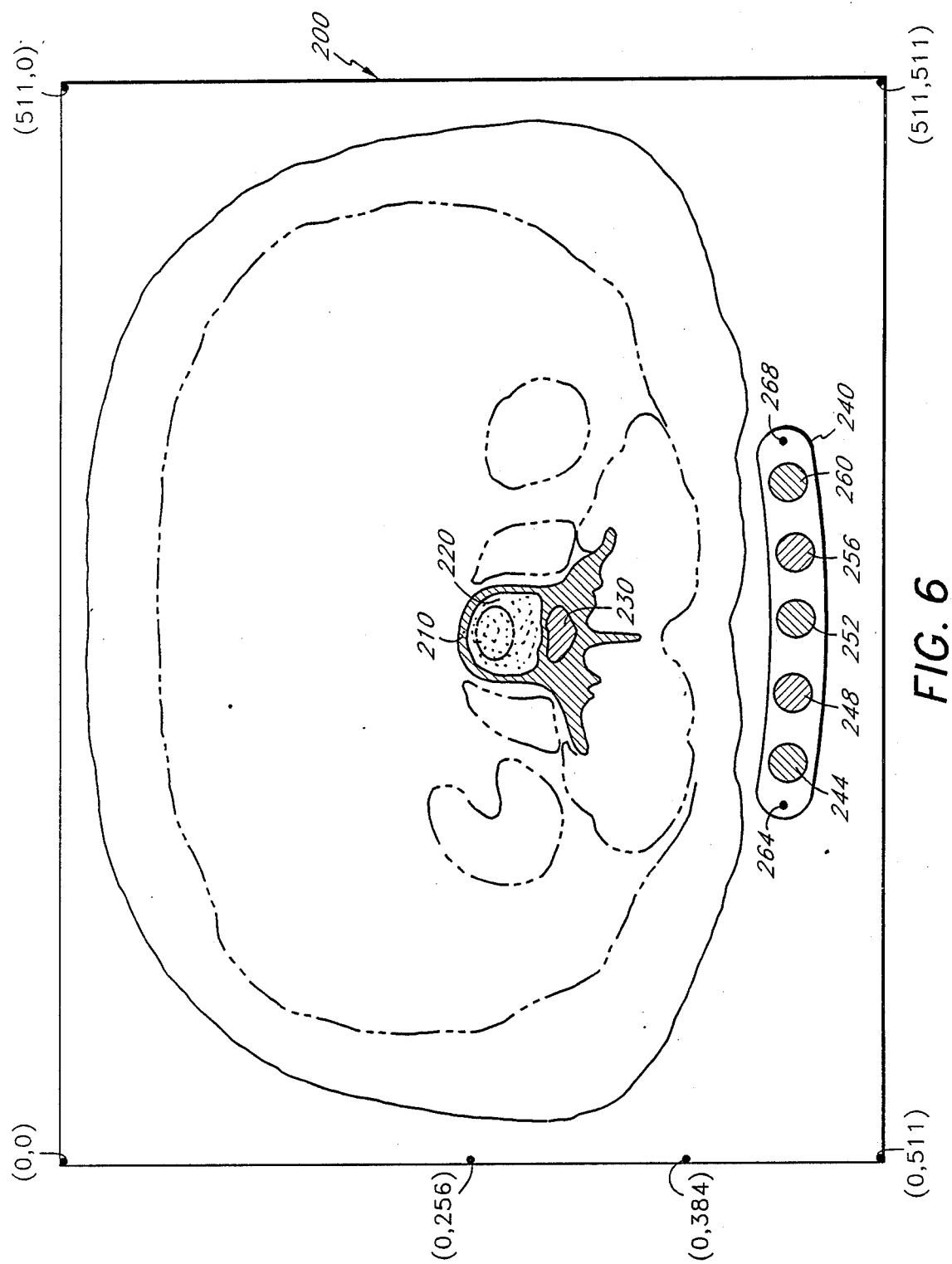
FIG. 6 is a view of an exemplary CT image of a patient and the calibration phantom produced by the CT system of FIG. 1, showing a cross-section of the internal structure of a patient's body positioned with respect to the calibration phantom.

As illustrated in FIG. 1, the patient 120 is positioned so that the patient's spine is proximate to the calibration phantom 116. The CT system is operated in a conventional manner to produce an image 200, illustrated in FIG. 6 as a video image such as is displayed on a video monitor. The image 200 represents a cross-section through the patient's body. As is well known in the art, such an image 200 comprises a plurality of pixels that each has an intensity that corresponds to the attenuation of the x-rays by the internal structure of the portion of the patient's body that has been scanned. In FIG. 6, the individual pixels are not shown because of their small size. For example, the image 200 advantageously comprises a matrix of 512 pixels in each horizontal row by 512 rows. Thus, the upper leftmost pixel is designated in a conventional manner as pixel 0,0 (i.e., pixel 0, row 0); the upper rightmost pixel is designated as pixel 511,0 (i.e., pixel 511, row 0); the lower leftmost pixel is designated as pixel 0,511 (i.e., pixel 0, row 511); and the lower rightmost pixel is designated as pixel 511,511 (i.e., pixel 511, row 511). As further examples, the pixel at the approximate center of the left boundary of the video image 200 is designated as pixel 0,256, and the pixel that is approximately three-fourths of the way down the left boundary of the video image 200 is designated as pixel 0,384. Of course, other conventions can be used. Also the number of pixels per row and the number of rows of pixels will vary in accordance with the spatial resolution of the particular CT apparatus in accordance with the number of storage locations allocated within the CT system computer for controlling the video display. It is of course understood that the CT system computer stores a digital representation of the image and that the following discussion with respect to the processing of the image refers to the digital representations of the image in the CT system computer.

In FIG. 6, the image 200 includes a representation of the cortical bone 210, a representation of the trabecular bone 220, a representation of the spinal cord 230, and representations of other internal body structures (shown in phantom outline). Because of the positioning of the calibration phantom 116, the image also includes a cross-section 240 of the calibration phantom 116, as illustrated in FIG. 6. The calibration phantom image 240 includes an image 244 of the first cavity 144, an image 248 of the second cavity 148, an image 252 of the third cavity 152, an image 256 of the fourth cavity 156, an image 260 of the fifth cavity 160, an image 264 of the first metallic rod 164, and an image 268 of the second metallic rod 168. As used herein, references to the images of the cavities are intended to mean images of the reference samples, as the reference samples provide the attenuation characteristics described herein, and the term cavity image is used interchangeably with the term reference sample image.

As is well known in the CT scanning art, the image that is produced includes areas of relatively high intensity corresponding to relatively high x-ray attenuation and areas of relatively lower intensity corresponding to relatively low x-ray attenuation. For example, in FIG. 6, the cortical bone image 210 will have a greater intensity than the intensity of the trabecular bone image 220. The trabecular bone image 220 will typically have a greater intensity than the spinal cord image 230. Similarly, the five cavity or reference sample images 244, 248, 252, 256, 260 have intensities that are proportional to the known concentrations of the reference samples within the cavities of the calibration phantom.

Figure 7:
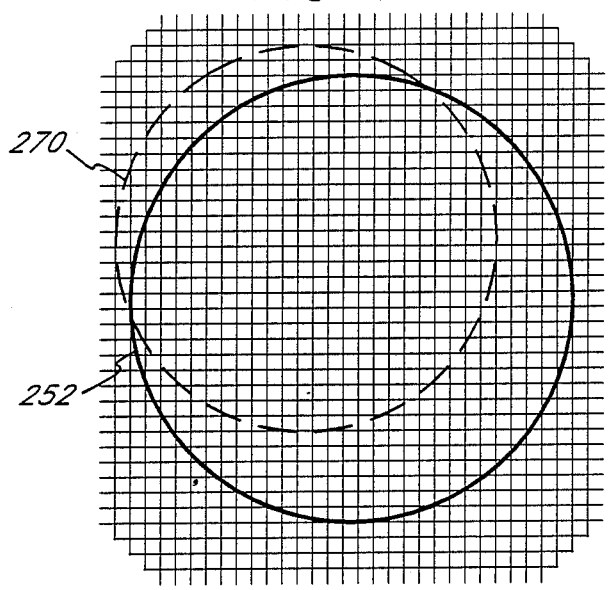
FIG. 7 illustrates an enlarged image of an exemplary reference sample of the calibration phantom with an improperly positioned region of interest superimposed thereon.
Figure 8:
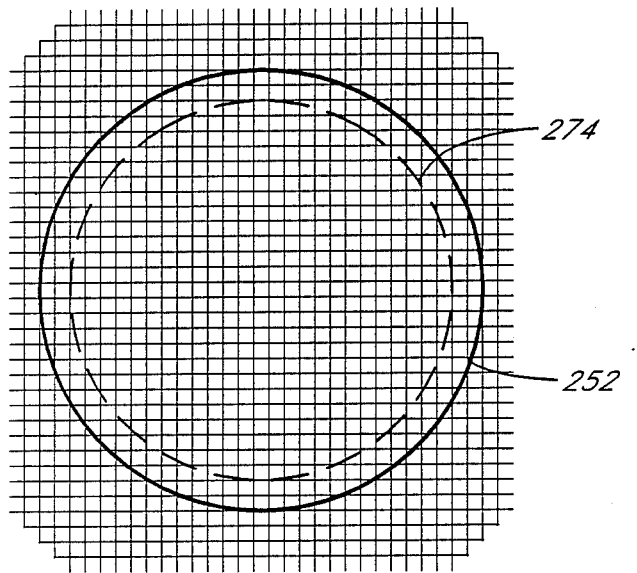
FIG. 8 illustrates an enlarged image of an exemplary reference sample of the calibration phantom with a properly positioned region of interest superimposed thereon.

In order to evaluate the mineral content of the patient's trabecular bone, it is necessary to determine the amount of attenuation of the x-rays by the trabecular bone, as represented by the trabecular bone image 220. The first series of steps involve determining the scale factors to be used to evaluate the trabecular bone image 220. This is accomplished by measuring the intensities of the reference sample images 244, 248, 252, 256, 260 and correlating the measured intensities with the known concentrations of the calibration materials within the reference sample cavities. The intensities are "measured" by the CT system computer by calculating the average intensities of the image pixels within the portions of the image that represent the reference samples using the stored digital representations of the reference sample images. However, in order to average the pixel intensities, the algorithms within the CT system computer must first be provided with the boundaries of the reference sample images so that the averaging is performed only with respect to pixels that are within the reference sample images. This requirement can be better understood by referring to FIG. 7 which is enlarged view of the reference sample image 252 of the reference sample within the third cavity 152. A first dashed circle 270 is superimposed over the third cavity or reference sample image 252 to represent a first region of interest to be evaluated by the algorithms within the CT system computer. In other words, the algorithms will cause the CT system computer to average the intensities of all the pixels within the boundaries of the first region of interest 270. As illustrated in FIG. 7, the first region of interest 270 includes pixels that lie within the third reference sample image 252. The first region of interest 270 also includes pixels that lie outside the third reference sample image 252 and thus represent portions of the image 240 of the body of the calibration phantom 116. Typically, the attenuation of the body of the calibration phantom 116 is less than the attenuation of the reference sample calibration materials within the third cavity 152. Thus, if pixels that lie outside the third reference sample image 252 are included in the calculation of the average intensity, the resulting average will be abnormally low. If the average is used as part of the regression analysis in the calculation of the scale factor, it may result in a scale factor that is too high. Thus, the measured intensities of the trabecular bone image 220 will be multiplied by too large a scale factor, and the calculated bone mineral content will be incorrect. Therefore, it is important that a region of interest be positioned entirely within the third reference sample image 252 as illustrated by a second region of interest 274 in FIG. 8. The regions of interest must also be accurately positioned for the other reference sample images.

Prior CT scanning systems have required the operator of the system to manually position a region of interest in each of the first, second, third, fourth and fifth reference sample images 244, 248, 252, 256, 260. This was a slow process that required careful sizing and positioning of the region of interest using the cursor control keys of a keyboard, a joy stick, a mouse, the entry of cursor coordinates, or the like. In any event, the positioning was subject to operator error and could result in incorrect and/or nonreproducible readings. Such incorrect readings could result in an incorrect diagnosis of the patient's condition or could require the patient to have to repeat the scanning procedure with increased radiation exposure.

Figure 9:
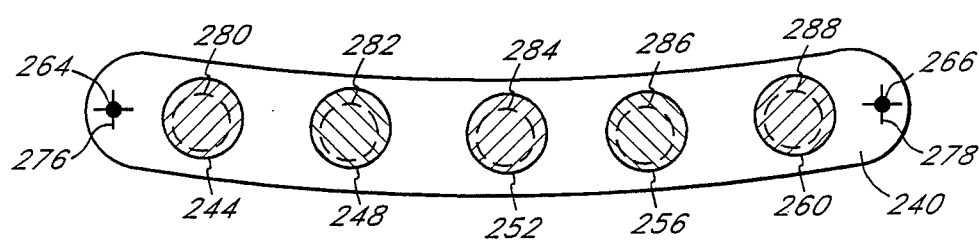
FIG. 9 illustrates a CT image of the calibration phantom showing cursors positioned on the images of the first and second localization metallic rods, and further showing regions of interest positioned within each of the reference sample images.

One of the first improvements in the procedure was to eliminate the necessity for the operator to position the regions of interest within the reference sample images. Instead, the first and second images 264 and 268 of the metallic rods were used as reference points in the image. As set forth above, the metallic rods 164 and 168 and the cavities 144, 148, 152, 156 and 160 are accurately positioned in the calibration phantom 116 so that the positions of the reference sample images can be readily calculated once the positions of the metallic rod images are accurately determined. Thus, in the first improved procedure, the operator of the system manually positioned a first cursor (or pointer) to the perceived center of the first metallic rod image 264 and positioned a second cursor in the perceived center of the second metallic rod image 268. This was accomplished by using a light pen, a trackball (i.e., mouse), cursor control keys, or the like. This is illustrated in FIG. 9 wherein a first cross-shaped cursor 276 and a second cross-shaped cursor 278 are shown positioned on the approximate centers of the first and second rod images 264 and 266, respectively. The algorithms within the CT system computer determined the X-Y coordinates of the centers of the rod images 264 and 268, and then calculated the centers of the reference sample images 244, 248, 252, 256, 260 from those coordinates. Thereafter, the CT system computer algorithms calculated a region of interest 280, 282, 284, 286, and 288, for each of the reference sample images 244, 248, 252, 256, and 260, respectively, that is centered on the respective calculated center of the reference sample image and has a size selected to encompass only pixels that are within the reference sample image.

Figure 10:
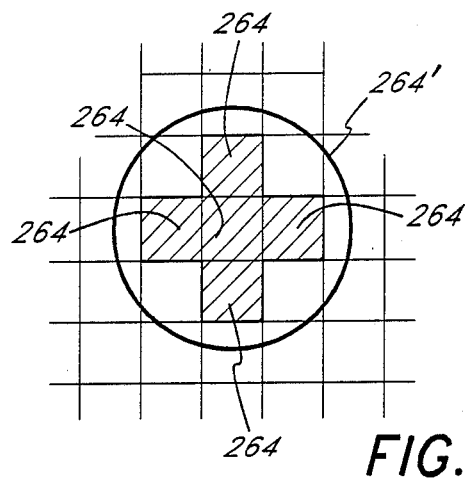
FIG. 10 is an enlarged view of the first rod image illustrating its composition as a plurality of pixels.

The use of the metallic rods 164, 168 was an improvement in the calibration phantom described above; however, the operator was still required to manually position a cursor at the center of each of the metallic rod images 264, 268. Typically, the metallic rods have relatively small diameters to reduce streaking and other image distortion caused by x-rays reflecting off the metallic rods. Thus, the metallic rod images 264, 268 are also small. For example, the cross-sections of the metallic rods may have diameters of approximately 2 millimeters, corresponding to the width of approximately three 0.6 millimeter wide pixels on an exemplary video display monitor. See, for example, FIG. 10, which is an enlarged view of the metallic rod image 264 superimposed on the pixels of a display monitor. The solid circle 264' represents the idealized circular image of the metallic rod, and the cross-hatched pixels 264 represent the image pixels that are at full intensity to represent the rod attenuation. The pixel at the intersection of the vertical column and horizontal row of cross-hatched pixels will be taken as the center of the first rod image 264. The pixels outside the cross-hatched area will have intensities that vary in accordance with the portion of the pixel that is attenuated by the rod. It can thus be seen that the positioning of the cursor in the centers of the metallic rod images is not an easy task for an operator and will be subject to some variation in the determined centers of the rod images that will be used for the localization of the reference sample images. If the operator fails to properly position the cursor at or near the center of each of the rod images, the positioning of the regions of interest within the reference sample images will also fluctuate. Thus, there would be some likelihood that the regions of interest in the reference samples will not be precisely reproducible. Furthermore, placement of the cursors is tedious and time consuming for the operator and uses valuable CT system operating time.

DESCRIPTION OF THE EMBODIMENT OF FIGS. 11 AND 12

Figure 11:
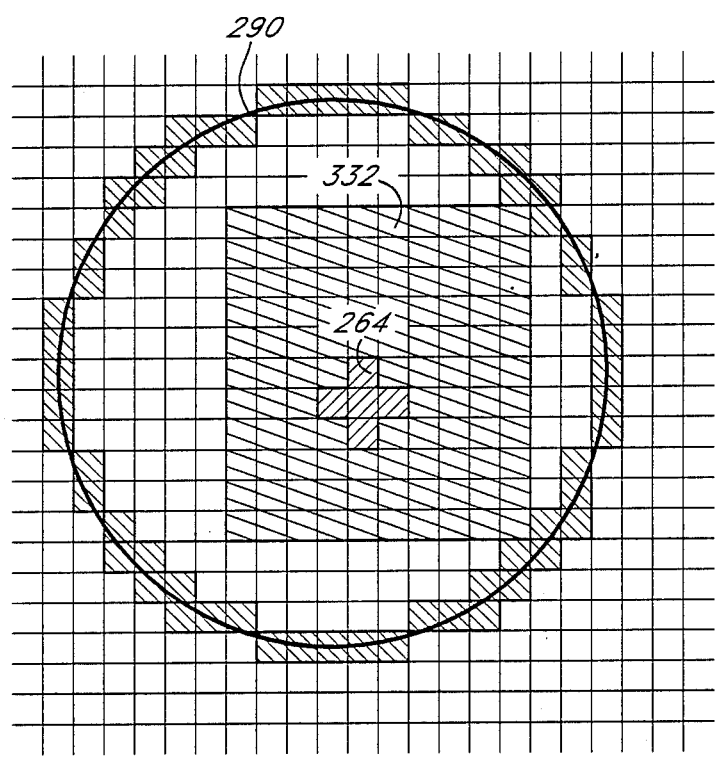
FIG. 11 illustrates the rod image of FIG. 10 with a large region of interest positioned around it, and further illustrating a smaller range of pixels that are evaluated to more precisely locate the center of the rod image.

One aspect of the present invention is a method for automatically locating the centers of the metallic rod images 264, 268. Rather than requiring the operator to manually position a cursor (e.g., the cross-shaped cursor 276 in FIG. 9) at the center of a rod image, the present invention requires no operator interaction to locate the center of the rod image. The algorithms of the present invention automatically process a relatively large region of interest 290 around the rod image, as illustrated in FIG. 11. (In FIG. 11, the idealized circular region of interest 290 is shown as comprising a plurality of pixels that are cross-hatched to indicate that they have a relatively high intensity compared to the background intensity of the body image 240.) Thereafter, an algorithm within the CT system computer sequences through the digital representations of the pixels within the computer-defined search region of interest 290 to find the pixels having intensities corresponding to the attenuation of the metallic rod 164. For example, in one embodiment of the invention, the algorithm searches for pixels having intensities that correspond to attenuations greater than 800 HU. When the pixels are found, the algorithm then calculates the center of the pixels in the metallic rod image 264 and stores the coordinates as one coordinate of the two reference coordinates. In one particularly preferred embodiment of this aspect of the invention, the center of the rod image 264 is calculated by selecting the pixel having the greatest intensity (i.e., the greatest attenuation) and presuming that the greatest attenuation corresponds to the center of the rod image 264. Thereafter, the algorithm automatically positions a second search region of interest around the second metallic rod image 268, and the algorithm finds the pixels representing the second metallic rod image 264, calculates the center of the second metallic rod image 268, and stores the coordinates as the second of the two reference coordinates. Thereafter, the algorithm uses the two reference coordinates to find the centers of the first, second, third, fourth and fifth reference sample images 244, 248, 252, 256, 260, measures the attenuations, performs regression analysis, and calculates the scale factor as was described above. This improved method is considerably more accurate and more rapid than the previously known manual method and results in more accurate and reproducible measurements, reduced examination times, and more efficient utilization of the CT system.

Figure 12:
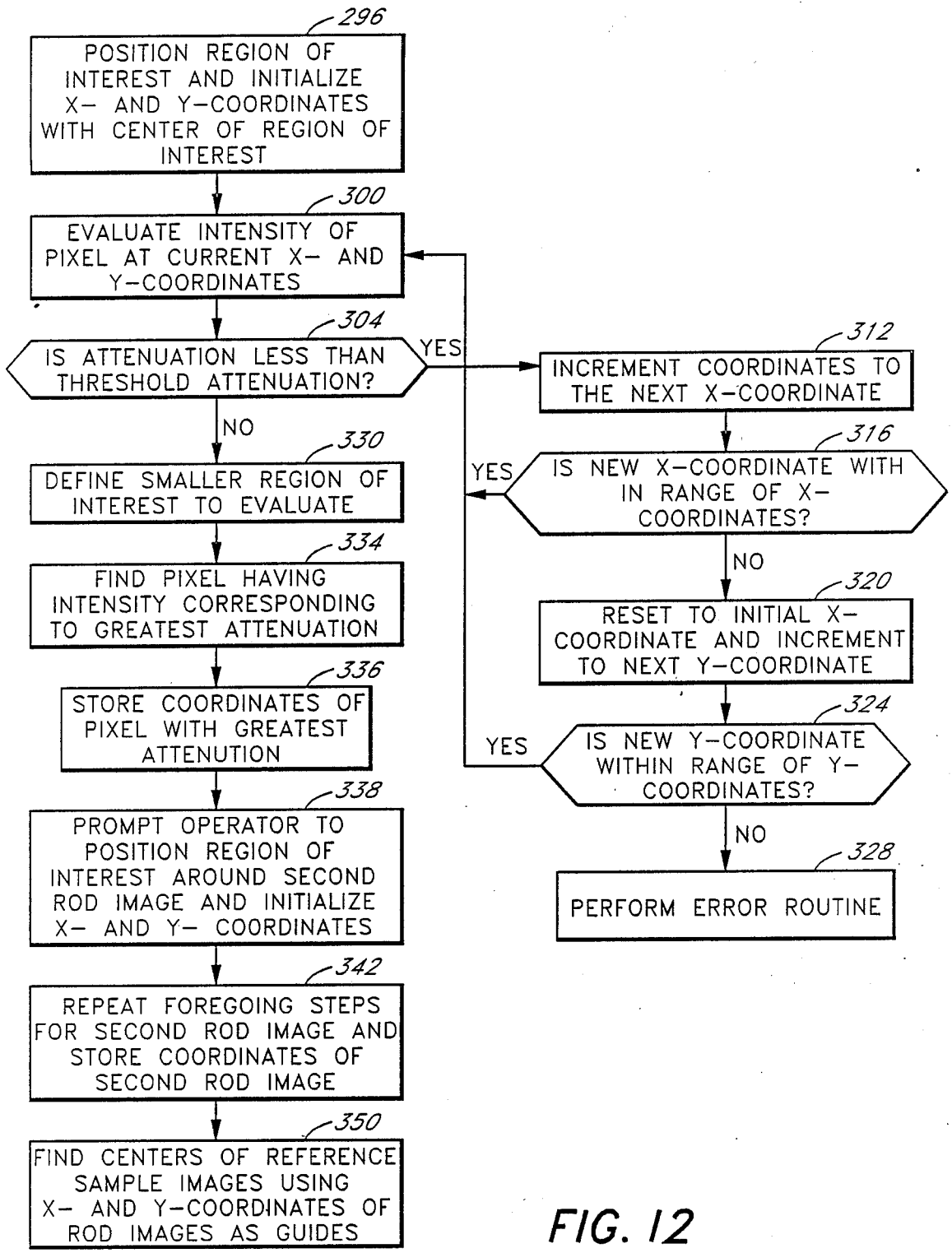
FIG. 12 is a flow chart of an improved method for locating rod images in a CT scan image by an automated method.

One method of performing the above-described task of finding the centers of the first and second metallic rod images 264 and 268 is illustrated by a flow chart in FIG. 12. The first task of the routine is to define the search region of interest in which to search for the first metallic rod image 264. In an activity block 296, the computer automatically positions the region of interest 290 around the first metallic rod image 264. The rod center finding routine then enters an activity block 300 with the coordinates of the center of the region of interest as positioned by the computer. In the activity block 300, the intensity of the pixel at the current X- and Y-coordinates is evaluated. In a decision box 304, the intensity (i.e., attenuation) is compared to the threshold attenuation for the metallic rods (e.g., the attenuation is compared to an attenuation of 800). If the attenuation is less than the threshold attenuation, as determined in the decision block 304, the X-coordinate is incremented to the next X-coordinate in an activity block 312. After incrementing the X-coordinate, the X-coordinate is checked in a decision block 316 to determine whether it is within the range of X-coordinates for the region of interest. If the X-coordinate is within the range, the process returns to the activity block 300 to determine the intensity of the next pixel defined by the new X-coordinate. If the next X-coordinate is outside the range of the region of interest, as determined in the decision block 316, then the X-coordinate is set back to the original X-coordinate and the Y-coordinate is incremented in an activity block 320. The new Y-coordinate is checked in a decision block 324 to determine whether it is outside the range of the region of interest, and if it is outside the range, the process proceeds to an error routine, represented by an activity block 328, to inform the operator that the region of interest was improperly placed or the image from the CT scanning process is unacceptable and gives the operator the option to manually position the cursors on the metallic rods. If the Y-coordinate is within the range of the region of interest, then the process continues in the activity block 300 where the intensity of the pixel defined by the new X- and Y-coordinates is evaluated as before.

Returning to the decision block 304, if the intensity of a pixel corresponds to an attenuation greater than the threshold attenuation, the process proceeds in an activity block 330 where the algorithm defines a smaller region of interest 332 centered on the pixel just evaluated. For example, in one embodiment, the region of interest is 11 pixels horizontally by 11 pixels vertically. Thereafter, the process evaluates each of the pixels in the small region of interest and finds the pixel having the greatest intensity (i.e., representing the greatest attenuation) as set forth in an activity block 334. The coordinates of this pixel are stored, in an activity block 336, as the coordinates of the center of the first metallic rod image 264. Thereafter, the computer positions a new search region of interest around the second metallic rod image 268, as represented by an activity block 338, and the foregoing steps are repeated for the second metallic rod image, as represented by an activity block 342 to find and store the coordinates of the center of the second metallic rod image 268. Thereafter, the routine is exited and the process finds the centers of the reference sample images and calculates the scale factor as was previously done in the above-described process, as represented by an activity block 350.

A further modification of the foregoing process is to fully automate the steps of finding the first and second metallic rod images 264 and 268. The modified process searches for the metallic rod images without requiring the operator to provide an initial region of interest. The process is basically the same as the process described above in connection with FIG. 12; however, the CT system computer algorithm initially defines a large region of interest in the lower portion of the video image where the phantom image 240 is most likely to be positioned. The algorithm then searches within that region of interest and finds the first and second metallic rod images 264 and 266, described above. Because of the small diameters of the metallic rods 164, 168, the search for rods can be slower than the manually assisted search described above. Further, the calibration phantom must be manufactured with the metallic localization rods which are precisely located with respect to the reference samples. This requires significant quality control in manufacturing the calibration phantoms. It is thus desirable to remove the rods completely from the calibration phantom. Thus, additional improvements, described below, have been made to increase the speed and accuracy of the invention.

Description of a An Alternative Embodiment of the Invention

Figure 13:
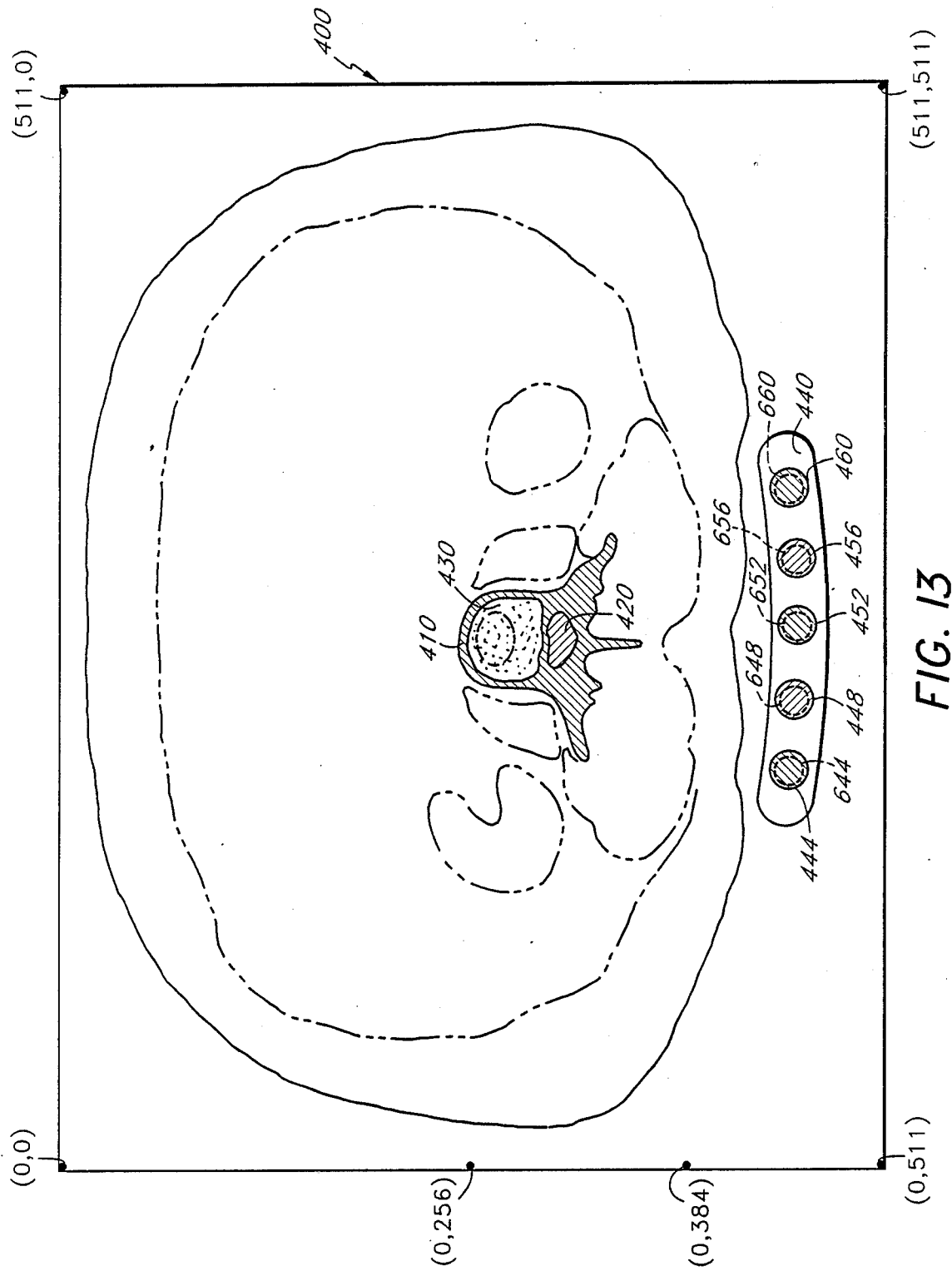
FIG. 13 is an exemplary CT scan image showing a cross-section of a person taken through one of the person's vertebrae and including an image of an improved version of the calibration phantom that contains no metallic rod localizing markers.
Figure 14:
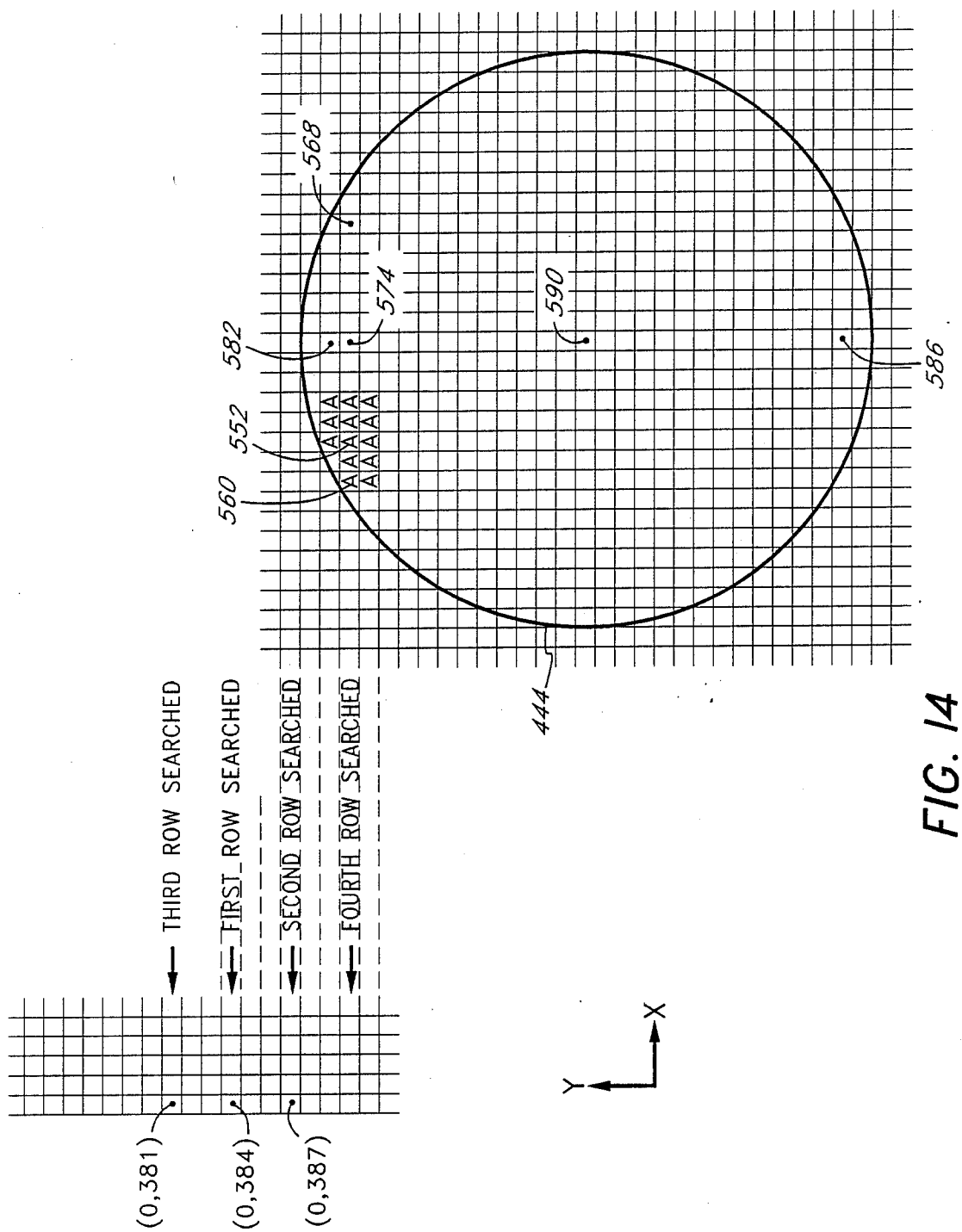
FIG. 14 is a broken enlarged view of a portion of the video image of FIG. 13 showing additional detail of the first reference sample image superimposed upon the pixels of the image.

FIGS. 13 and 14 illustrate an alternative embodiment of the present invention in which the localization of the phantom image boundaries and the reference sample images 244, 248, 252, 256, 260 is fully automated, both to decrease the amount of time required to locate the reference sample images and to increase the accuracy of the localization of the reference sample images.

FIG. 13 illustrates an exemplary video image 400 of a CT slice, such as was described above in connection with FIG. 6. In FIG. 13, the portions of the video image 400 are numbered similar to the corresponding portions of the video image 200 of FIG. 6; however, each of the numbers has been increased by 200. For example, the cortical bone 210 of FIG. 6 is designated as the cortical bone 410 in FIG. 13. FIG. 13 includes a calibration phantom image 440. The calibration phantom image 440 is illustrated as before; however, without the first and second metallic rod images which are not needed in the embodiment to be described below.

In the present invention, the CT system computer includes an algorithm that finds the reference sample images 444, 448, 452, 456, 460 automatically without requiring operator interaction. This process is significantly faster because it is known that the phantom image 440 in a properly performed CT scanning procedure will be located in the lower half of the video image 400. It is further known that the reference sample images 444, 448, 452, 456, 460 have predetermined attenuations (i.e., image intensities) and predetermined geometries and sizes (e.g., the reference sample images in FIGS. 13 and 14 advantageously have circular cross-sections with diameters in the range of 17-23 millimeters). Thus, the algorithm causes the CT system computer to search the video image for the reference sample images, as will be described below.

FIG. 14 illustrates a broken enlarged view of the video image 400 of FIG. 13, showing the first reference sample image 444 superimposed on the pixels of the video image 400. As illustrated in FIG. 14, an exemplary first reference sample image 444 has a diameter of approximately 17 millimeters. Thus, the first reference sample image 444 is shown as encompassing a pixel image having a diameter of approximately 28 0.6-millimeter pixels. It should be understood that pixels entirely within the boundary of the first reference sample image 444 have intensities corresponding to the attenuation of the first reference sample 144 (e.g., approximately −100 HU), and that pixels fully outside the boundary of the first reference sample image 444, representing the phantom body image 440, have intensities corresponding to the attenuation of the surrounding body of the calibration phantom (e.g., approximately 30 HU). Pixels that are part of the boundary between the first reference sample image 444 and the surrounding image of the calibration phantom have intensities in a range between the intensity of the first reference sample image 444 and the intensity of the surrounding body image 440 in accordance with the proportions of the reference sample 144 and the body 140 represented by the pixel.

Also shown in FIG. 14 is a portion of the left boundary of the video image that includes the pixel 0,384. As discussed above, the pixel 0,384 is approximately at the left boundary of the image and at the approximate vertical center of the lower half of the video image 400. Thus, since the calibration phantom image 440 is located in the lower half of the video image 400 when the CT scanning system is operated properly, the pixel 0,384 provides a starting location for the search for the phantom image and the reference sample images. Other pixels could of course be used for the starting location. For example, in one embodiment, the pixel 0,376 is used as the starting location.

Figure 15A:
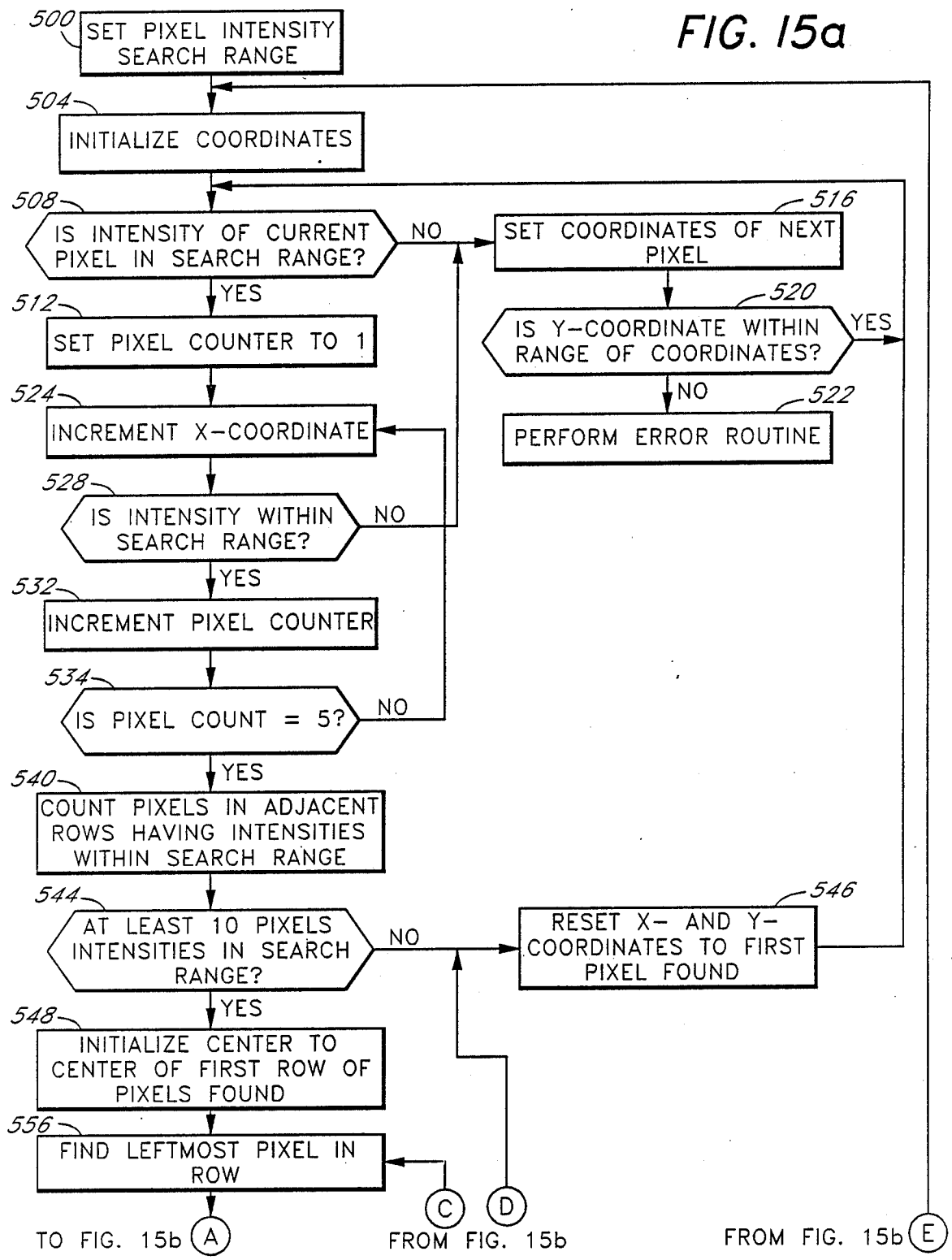
FIGS. 15a, 15b and 15c together illustrate a flow chart of the steps of an improved automated method of locating the reference sample images.
Figure 15B:
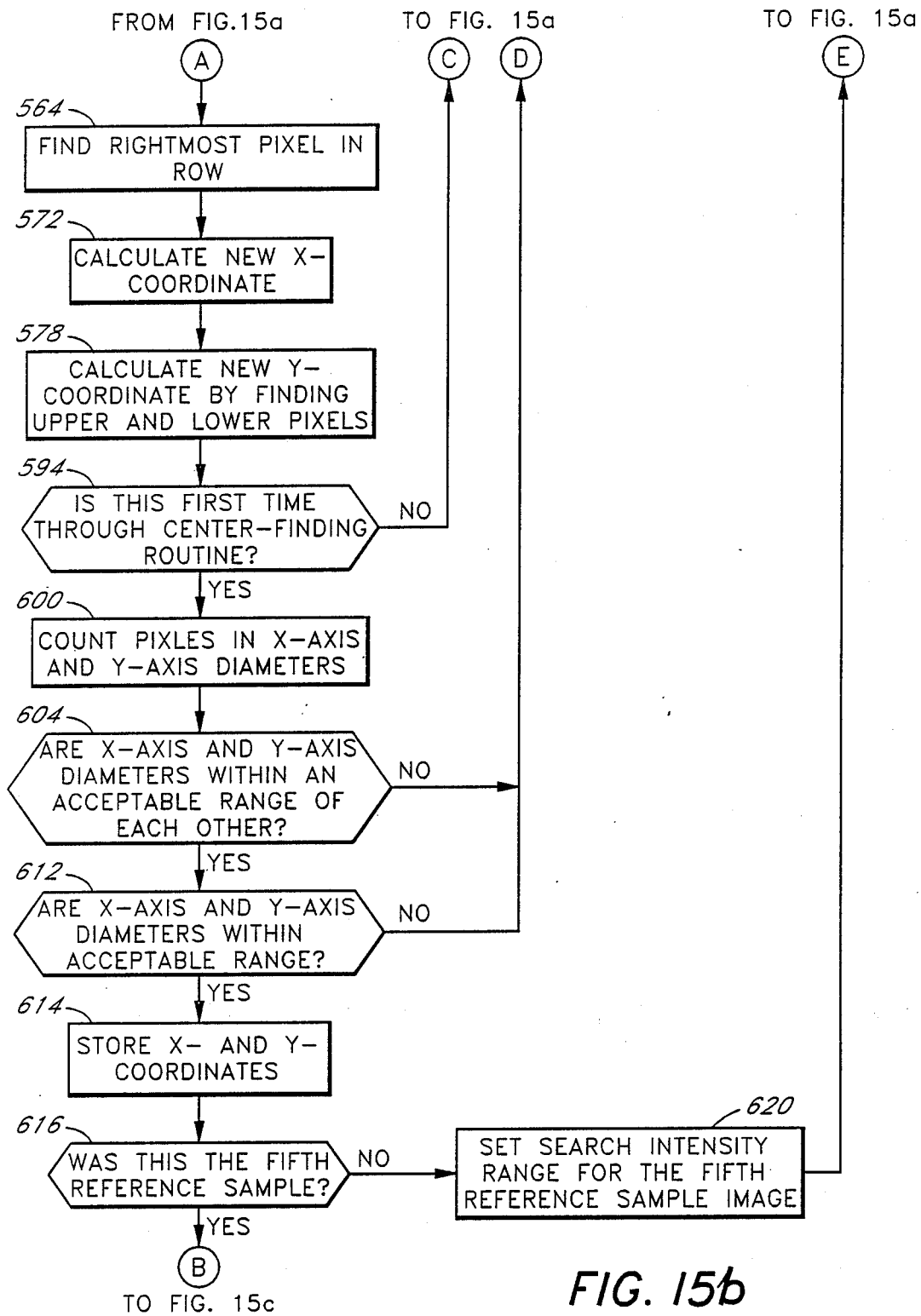
Figure 15C:
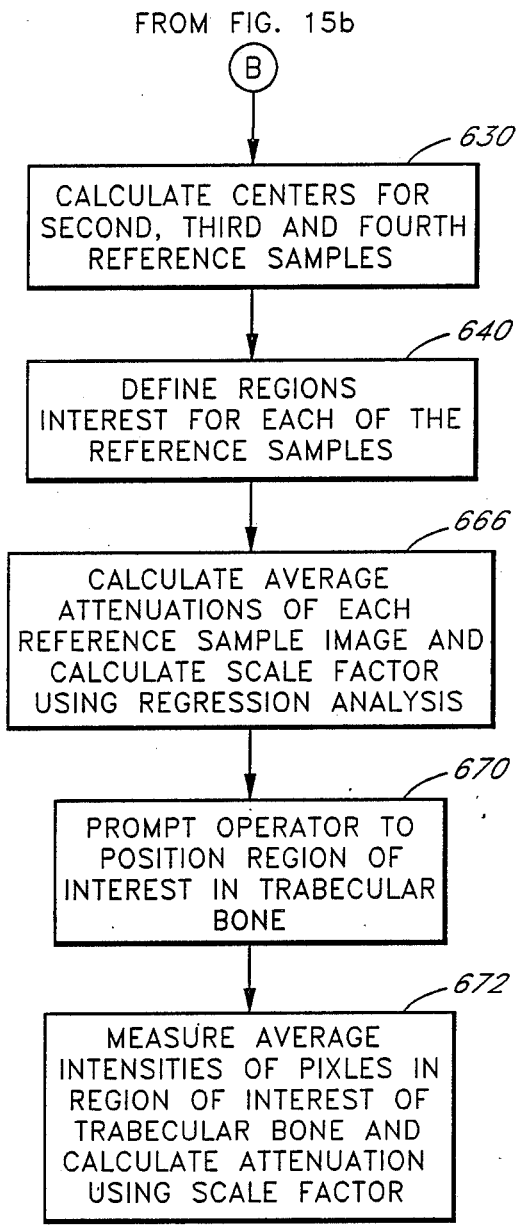

In the present invention, the CT system computer includes a search algorithm that initiates a search beginning at, for example, the pixel 0,384 and scans the pixels of the lower half of the video image 400 until it finds one of the reference sample images. In one preferred embodiment of the present invention, the search procedure first finds the first reference sample image 444 and then finds the fifth reference sample image 460. The searching algorithm is described below in connection with the flow chart in FIGS. 15a, 15b and 15c. In FIGS. 15a, 15b and 15c, the portions of the flow chart are connected between the three figures by using circles with letters therein. It should be understood that a line terminating at a lettered circle in one of the three figures continues at the corresponding lettered circle in another figure.

The searching algorithm begins with an activity block 500 in FIG. 15a, wherein the pixel intensity search range is set for a range of intensities that represents one of the reference sample images 444, 448, 452, 456, 460. For example, in one exemplary embodiment, the intensity search range is set for −100 HU so that the search algorithm will search for the first reference sample image 444 (i.e., the algorithm first searches for the reference sample image representing the reference sample having the least attenuation). Since the pixels representing the reference sample image can have a range of intensities caused by a number of factors, including image noise, the intensity search range is preferably set, for example, to −100±65 HU to accommodate expected variations in the attenuation. Of course, it is understood that the search algorithm can be modified to first search for one of the other reference sample images, such as the fifth reference sample image 460. After setting the intensity range, the algorithm continues in an activity block 504 wherein the coordinates of the search are initialized to the coordinates of the pixel 0,384. It is of course understood that the coordinates correspond to an address of a storage location in the data storage memory of the CT system computer where the digital representation of the pixel intensity is stored. Thereafter, the algorithm enters a decision block 508 wherein the digital representation of the intensity of the currently addressed pixel is compared to the intensity search range, thereby determining whether the pixel potentially represents a portion of the reference sample image that the algorithm is currently trying to locate. If the pixel intensity is within the search range, the algorithm then proceeds with the steps in an activity block 512, to be described below. Otherwise, if the pixel intensity is not within the search range, the algorithm continues with an activity block 516. In the activity block 516, the X-coordinate and the Y-coordinate for the next pixel to be examined are set. Although the search algorithm can examine every pixel, in preferred embodiments of the present invention, the speed at which the algorithm searches is enhanced by selectively examining spaced apart pixels. For example, in one particularly preferred embodiment of the present invention, the algorithm examines every third pixel in each horizontal row. In other words, the X-coordinate is incremented by three after the current pixel is examined. Since the first reference sample image 444 has a pixel diameter of approximately 28 pixels, the search algorithm cannot skip past the entire first reference sample image by searching in this manner. After an entire row of pixels has been examined, the Y-coordinate is also changed so that the next pixel to be searched is in a new row. At the same time, the X-coordinate is set back to zero, to the first coordinate in the new row. As with the X-coordinate, the Y-coordinate is preferably changed by more than one value (e.g., by three) to increase the rate at which the searching is performed. Also preferably, the Y-coordinate is not incremented each time. Rather, since the search algorithm begins in the center of the lower half of the video image 400, the algorithm first increments the Y-coordinate by three to search three rows below the initial search row, and then decrements the initial Y-coordinate by three to search three rows above the initial search row. Thereafter, the algorithm will search six rows below the initial search row and then six rows above the initial search row, and so on. Thus, the algorithm searches an area that expands outwardly from the center row of the lower half of the image, the most likely location for the phantom image 440.

After selecting the next X-coordinate and the next Y-coordinate, the algorithm enters a decision block 520 wherein the current Y-coordinate is compared with the range of Y-coordinates of the video image 400 (i.e., the Y-coordinate is greater than 0 and less than or equal to 511). If the Y-coordinate is outside the range, the search algorithm exits to an error routine, represented by an activity block 522 to inform the operator that the reference sample image 444 was not found and that the calibration procedure must be performed manually, such as was described above, or that the scanning operation must be repeated to provide a better video image 400. If the Y-coordinate is within the range of Y-coordinates, the algorithm continues in the decision block 508 where the intensity of the currently addressed pixel is compared to the search range as discussed above.

In the activity block 512, which is entered when a pixel is determined to have an intensity within the search range, the algorithm begins searching every pixel following the currently addressed pixel to determine whether the currently addressed pixel is actually within the first reference sample image 444. The portion of the routine represented by the activity block 512 is included to assure that the current pixel does not represent an artifact signal such as commonly occur in a CT scanning procedure. Thus, in the activity block 512, a pixel counter is set to 1. Thereafter, the X-coordinate is incremented by one pixel in an activity block 524 and then the algorithm enters a decision block 528 wherein the intensity of the then currently addressed pixel is compared to the search range. If the intensity is not within the search range, then the algorithm resumes the search portion of scanning by entering the activity block 516, described above. Otherwise, the algorithm enters an activity block 532 wherein the pixel counter is incremented by one count. Thereafter, the algorithm enters a decision block 534 wherein the pixel counter is checked to see if it is equal to five counts. If it is not equal to five counts, the algorithm returns to the activity block 524 to increment the X-coordinate and then the decision block 528 to compare the intensity of the next pixel to the search range. If five adjacent pixels are found that have intensities within the search range, then the algorithm goes from the decision block 534 to an activity block 540 wherein the algorithm begins examining the pixels in the adjacent rows to verify that the first five pixels just found are not part of a "streak" or other artifact in the video image. The algorithm first compares the intensities of the five pixels immediately above the first five pixels and counts the number of pixels having intensities within the search range. It then compares the intensities of the five pixels immediately below the first five pixels and counts the number of pixels having intensities within the search range. If at least ten of the fifteen pixels examined in the three adjacent rows have intensities within the search range, then the algorithm initially assumes that the pixels are within the boundaries of the first reference sample image 444. This is illustrated in FIG. 14 wherein thirteen pixels in the upper left hand portion of the first reference sample image 444 are labelled with the letter "A"" to indicate that the intensities were found to be within the search range. The count is compared with the acceptable count in a decision block 544. If the count is too low, the algorithm resumes searching in an activity block 546 by resetting the X-coordinate and the Y-coordinate to the coordinate of the first pixel found having an intensity within the acceptable range. The algorithm then continues with the activity block 516 where the coordinates are selectively changed to correspond to the next pixel to be searched, as described above.

If, in the decision block 544, it is determined that the number of adjacent pixels having intensities within the search range is at least ten, then the algorithm enters an activity block 548 wherein the algorithm searches for the center of the first reference sample image 444. In the activity block 548, the algorithm initially sets the coordinates of the center of the first reference sample image 444 to the coordinates of the center pixel of the first five pixels found as described above. For the example described above, the pixel is the pixel having the numeric designator 552 in FIG. 14. Since the first five pixels found are most like to be near the circumference of the first reference sample image 444, rather than being near the center, the algorithm then begins searching for the center of the first reference sample image 444 in accordance with the steps described hereinafter. The first step after setting the initial center coordinates is represented by an activity block 556 wherein the algorithm first searches for the leftmost pixel that is in the same row as the initially chosen pixel and that has an intensity within the search range. In the example illustrated in FIG. 14, the leftmost pixel having the appropriate intensity is a pixel 560. It should be understood that the pixel to the immediate left of the pixel 560 includes part of the phantom body image 440 and thus most likely has an intensity outside the search range. The next step, represented by an activity block 564 in FIG. 15*b*, finds the rightmost pixel in that same row that has an intensity within the search range. A pixel 568 satisfies that criteria. The next step, represented by an activity block 572, is to calculate a new X-coordinate $X_2$ for the center of the first reference sample image 444. This is accomplished by averaging the X-coordinate $X_{L1}$ of the leftmost pixel 560 and the X-coordinate $X_{R1}$ of the rightmost pixel 568 as follows:

$$X_2 = \frac{X_{L1} + X_{R1}}{2} \tag{1}$$

A pixel 574 having an X-coordinate with the integer value of the $X_2$ calculated in accordance with Equation (1) is shown in FIG. 14.

The next step, represented by an activity block 578, is to find the pixel closest to the center of the first reference sample image 444 in the Y-direction. The algorithm finds the uppermost pixel in the same column as the pixel 574 and having an intensity within the search range, for example, a pixel 582 in FIG. 14. The algorithm determines its Y-coordinate $Y_{U1}$. Similarly, the algorithm finds the Y-coordinate $Y_{L1}$ of a pixel 586 which is the lowermost pixel in the same column having an intensity within the search range. A new Y-coordinate $Y_2$ is calculated in the activity block 578 as the average of the uppermost Y-coordinate $Y_{U1}$ and the lowermost Y-coordinate $Y_{L1}$ as follows:

$$Y_2 = \frac{Y_{L1} + Y_{U1}}{2} \tag{2}$$

A new Center pixel 590, having the X-coordinate $X_2$ and the Y-coordinate $Y_2$ is thus defined. It is possible that the new center pixel 590 is not as close to the center of the first reference sample image 444 as it could be. Thus, the preferred embodiment of the present invention repeats the above-described center finding steps with the new X-coordinate $X_2$ and the new Y-coordinate $Y_2$ as the starting coordinates. This iterative center search portion of the algorithm is represented by a decision block 594 in which an iteration count is examined to determine whether the algorithm has passed through the center-finding algorithm twice. If only one iteration has been performed, the algorithm returns to the activity block 556 in FIG. 15*a* to again calculate new X- and Y-coordinates in the manner just described. The pixel found in the second iteration may be the same pixel that was found in the first iteration.

If two iterations of the center finding steps have been performed, the algorithm then continues with the steps in an activity block 600 wherein the X-axis diameter and the Y-axis diameter of the first reference sample image 444 are checked to see if they are substantially the same to verify the geometric shape of the reference sample image. In the activity block 600, the number of pixels in the same horizontal row as the center pixel 590 and having intensities within the search range are counted to determine the X-axis diameter. Similarly, the number of pixels in the same vertical column as the center pixel 590 are counted to determine the Y-axis diameter. In a decision block 604, the X-axis diameter is compared to the Y-axis diameter. If the two diameters are within an predetermined acceptable range of each other, for example, within three pixels of each other, the algorithm continues in a decision block 612. Otherwise, if the two diameters are not sufficiently close to each other in magnitude, it is assumed that the algorithm found a portion of the body structure or something other than the center of the first reference sample image 444, and the algorithm resumes the search portion of the routine via the activity block 546 in FIG. 15*a*, wherein the X-coordinate and the Y-coordinate are reset back to the coordinates of the original pixel found in the search procedure. Thereafter, the searching resumes through the activity block 516, as described above.

If the two diameters are within the predetermined acceptable range of each other, the algorithm continues in a decision block 612 wherein the X-diameter and the Y-diameter calculated in the activity block 600 are compared to the range of known diameters of the first reference sample image 444. For example, the first reference sample image may have an expected range of diameters from 17 to 24 millimeters, corresponding to a pixel diameter range of 28 to 40 pixels, depending upon the magnification of the image on the video display. If the calculated diameters are outside the range, the algorithm resumes the search portion via the activity blocks 546 and 516 in FIG. 15*a*, as described above. Otherwise, if the calculated diameters are within the acceptable range, the algorithm continues in an activity block 614 wherein the X-coordinate and the Y-coordinate are stored as the X-coordinates and the Y-coordinates of the first reference sample image 444. Thereafter, the algorithm enters a decision block 616 wherein the it is determined whether the algorithm was searching for the first reference sample image 444 or the fifth reference sample image 460. If the algorithm was searching for the first reference sample image, then the algorithm enters an activity block 620 wherein the intensity search range is set for the expected intensity range of the fifth reference sample image 460. Thereafter, the algorithm returns to the activity block 504 in FIG. 15*a*, wherein the algorithm repeats the above-described steps for the fifth reference sample image 460 to find and store the X-coordinate and the Y-coordinate of the center of the fifth reference sample image 460. After completing the steps for the fifth reference sample image, the algorithm enters an activity block 630 in FIG. 15*c*, wherein the coordinates of the centers for the second, third and fourth reference sample images are calculated, such as was previously done in the prior art. Thereafter, in an activity block 640, a region of interest is defined for each of the reference sample images. The regions of interest are preferably displayed on the video image 400 as circles 644, 648, 652, 656, and 660, as illustrated in FIG. 13 to provide a visual indication that the automatic search procedure had finished and to allow the operator to verify that the positioning of the regions of interest are acceptable. After defining the regions of interest 644, 648, 652, 656, 660, the average attenuations of the pixels within the regions of interest are calculated and the scale factor calculated, as previously described, in an activity block 666.

The algorithm then enters an activity block 670 and requests the operator to define a region of interest for the trabecular bone so that the mineral content of the trabecular bone can be determined as described above. For example, the CT system computer includes an algorithm, represented by an activity block 672, that averages the intensities of the pixels within the defined region of interest to calculate an average attenuation. Thereafter, the average attenuation is multiplied by the scale factor determined above. The measured average intensity is then compared to the attenuations that correspond to various concentrations of mineral content for the trabecular bone and a number corresponding to the mineral content is provided as a visual output to the operator as well as being recorded as part of the permanent record of the patient.

Figure 16:
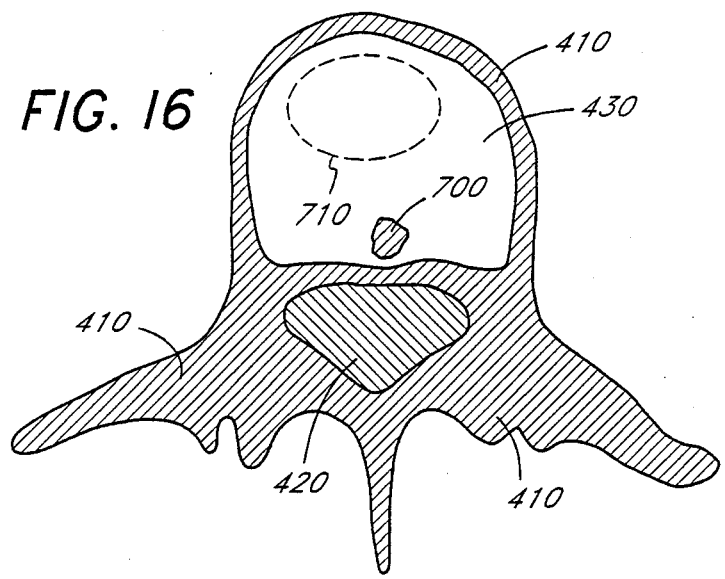
FIG. 16 is an enlarged view of the vertebral body, including the cortical bone, trabecular bone and spinal cord of FIG. 13, and showing an enlarged elliptical region of interest that is positionable by an operator to encompass a large portion of the trabecular bone.

Description of Improved System for Automatically Establishing Region of Interest in Image of Trabecular Bone FIG. 16 illustrates the video image 400 of FIG. 13, showing the cortical bone image 410, the spinal cord image 420 and the trabecular bone image 430 in enlarged cross-section. In FIG. 16, an image 700 of the basivertebral vein is also shown. As set forth above, the known CT scanning systems require the operator to accurately place a region of interest within the area of the trabecular bone image 430. Typically, the region of interest is an area defined by an ellipse, such as an ellipse 710, shown in dashed lines in FIG. 16. In order to accurately calculate the average attenuation of the trabecular bone, and thus calculate the mineral content of the trabecular bone, it is preferable to include a large portion of the trabecular bone image 430 within the area encompassed by the region of interest ellipse 710. At the same time, since the attenuation of the cortical bone is substantially greater than the attenuation of the trabecular bone, it is important that the region of interest ellipse 710 not include any of the cortical bone image 410 within its boundaries. Thus, the region of interest ellipse 710 is kept substantially smaller than the inner boundary of the cortical bone image 410 so that there is no overlap. Also, it is generally preferable that the basivertebral vein image 700 not be included within the boundary of the region of interest ellipse 710 since it typically has a lower attenuation than the trabecular bone image 430. In any event, the operator of the CT scanning system has heretofore been required to manually position the region of interest ellipse 710 within the boundaries of the cortical bone image 410 so that it encompasses only the trabecular bone image 430. Just as in the previously discussed manual placements of the regions of interest, the manual placement of the region of interest ellipse 700 is a slow process and is subject to improper placement by the operator. Thus, one aspect of the present invention includes an improved method for correctly placing the region of interest so that little operator intervention is required and so that the consistency and reproducibility of the positioning is increased.

Figure 17:
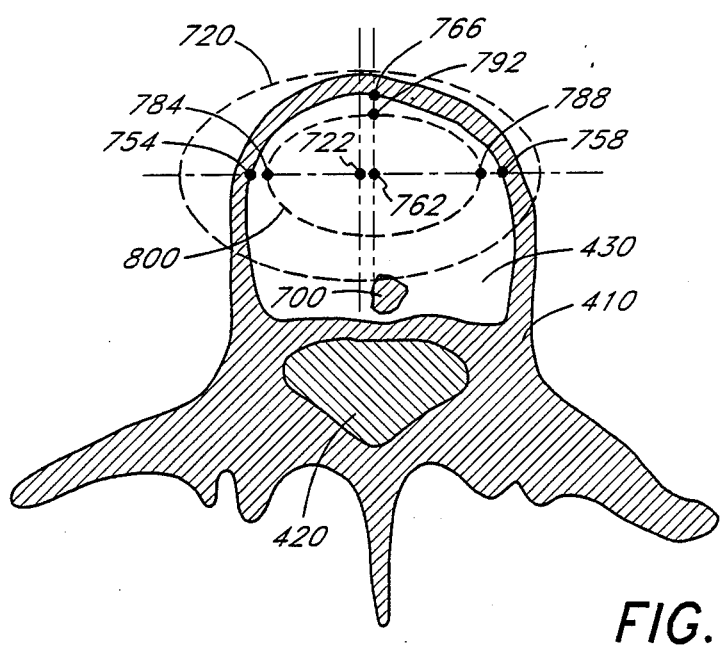
FIG. 17 is a view of the vertebral body, similar to FIG. 16, illustrating an enlarged search region of interest and a reduced region of interest generated and automatically positioned by the present invention.
Figure 18:
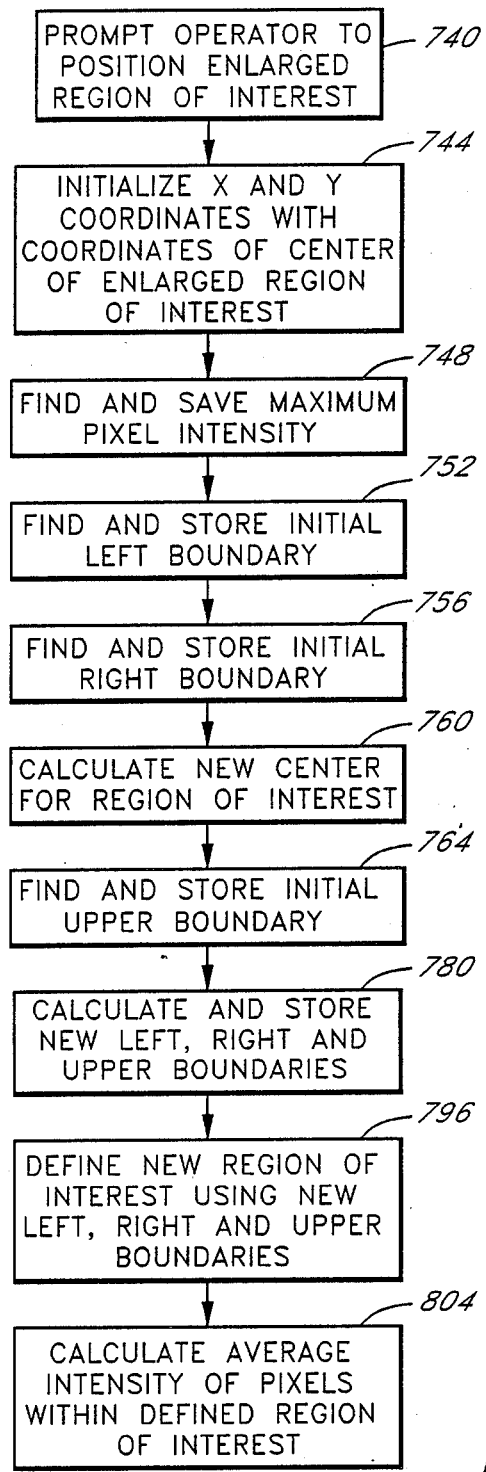
FIG. 18 is a flow chart illustrating the method of generating the reduced region of interest of FIG. 17.

In FIG. 17, the cortical bone image 410, the spinal cord image 420, the trabecular bone image 430 and the basivertebral vein image 700 are again illustrated. In FIG. 17, an enlarged region of interest 720 is illustrated. The enlarged region of interest 720 is generated by the CT system computer and is preferably sufficiently large to encompass the entire upper region of the vertebral body, including the trabecular bone image 430 and a substantial portion of the cortical bone image 410, proximate to the trabecular bone image 430. Although shown as an ellipse in FIG. 17, the enlarged region of interest can be a rectangle, a square, or other geometric shape. The operation of the CT system computer in placing a region of interest within the boundary of the trabecular bone image 430 is described hereinafter in connection with a flow chart illustrated in FIG. 18. In an activity block 740 in FIG. 18, the operator is prompted to position the enlarged region of interest 720 so that it encompasses the entire top region of the vertebral body including the trabecular bone image 430. Preferably, the center of the enlarged region of interest 720 is within the trabecular bone image 430.

After the operator has positioned the enlarged region of interest, an activity block 744 is entered wherein the algorithm within the CT system computer initializes the X-coordinate and the Y-coordinate of a search routine with the center 722 of the enlarged region of interest 720. Thereafter, in an activity block 748, the algorithm searches vertically, from the bottom of the enlarged region of interest ellipse 720 to the top of the ellipse 720 along a line passing through the initial center 722 to find the maximum pixel intensity, corresponding to the maximum attenuation of the cortical bone image 410. Thereafter, in an activity block 752, the algorithm scans horizontally, for example to the left, from the initial center 722 until it detects a pixel having an attenuation that is within 100 HU of the previously detected maximum attenuation. This pixel is presumed to represent the boundary between the trabecular bone image 430 having lower attenuations and the cortical bone image 410 having higher attenuations. The coordinates of this pixel are stored as an initial left boundary 754 of the trabecular bone image 430. In an activity block 756, the algorithm searches in the opposite horizontal direction, for example to the right, from the initial center 722 until it detects a pixel having an attenuation that is within 100 HU of the maximum attenuation. The coordinates of this pixel are stored as an initial right boundary 758 of the trabecular bone image 430. In an activity block 760, the algorithm calculates a new horizontal center 762 that is halfway between the above-detected left and right boundaries. Then, in an activity block 764, the algorithm searches vertically upwardly from the new horizontal center 762 until a pixel is detected that has an intensity corresponding to an attenuation of 100 HU less than the maximum attenuation. The coordinates of this pixel are stored as an initial upper boundary 766 of the trabecular bone image 430.

After the initial left, right and upper boundaries are determined as just described, the boundaries for a region of interest is defined in an activity block 780. Rather than using the initial boundaries directly, the algorithm defines a new set of boundaries that are a predetermined number of pixels into the trabecular bone image 430 away from the cortical bone image 410. For example, in one embodiment, a new left boundary 784 is defined as a pixel that is five pixels to the right of the initial left boundary 754. Similarly, a new right boundary 788 is defined as a pixel that is five pixels to the left of the initial right boundary 758, and a new upper boundary 792 is defined that is five pixels below the initial upper boundary 766. Then, in an activity block 796, a new elliptical region of interest 800 is defined that has its horizontal vertices at the new left boundary 784 and at the new right boundary 788, and has one vertical vertex at the new upper boundary 792. It should be understood that the two horizontal vertices 784 and 788 and the one vertical vertex 792 are sufficient to define an ellipse through the vertices. The elliptical region of interest 800 will be solely within the trabecular bone image 430 since its vertices 784, 788 and 792 are within the trabecular bone image 430.

After defining the new region of interest 800, as described above, the algorithm then proceeds to calculate the average attenuation of the pixels within the defined region of interest 800 in a conventional manner, as illustrated by an activity block 804.

Figure 19:
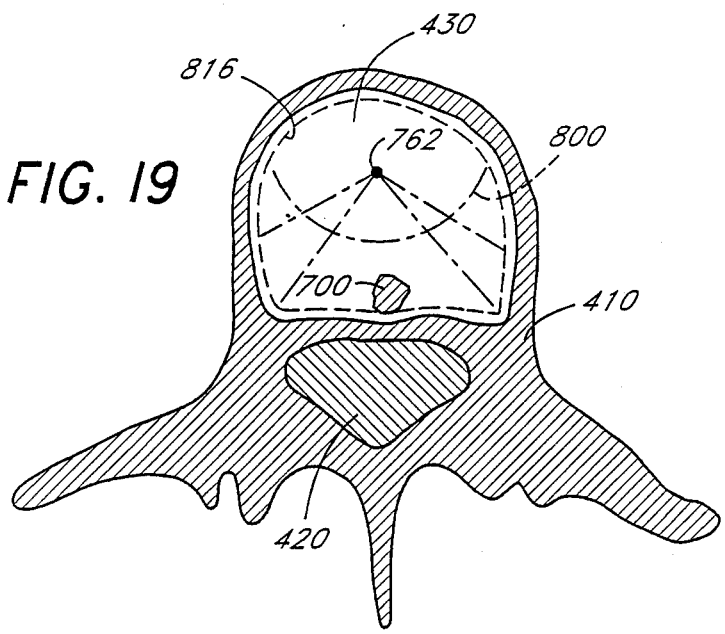
FIG. 19 is a view similar to FIG. 16 illustrating an alternative geometrically shaped region of interest generally conforming to the boundaries of the trabecular bone region of the image.

A further improvement to this aspect of the present invention is illustrated in FIG. 19. In FIG. 19, the new region of interest 800 is illustrated as in FIG. 17. After determining the boundaries of the new region of interest 800, as described above, the CT system computer can advantageously evaluate the pixels along lines radiating outwardly from the center 762 of the region of interest 800 until pixels having attenuations outside the expected range of the attenuation of the trabecular bone image 430 are detected. For example, this is advantageously accomplished by detecting pixels having an attenuation within 100 HU of the attenuation of the cortical bone image 410, as described above. In this manner, a new region of interest 816 generally conforming to the complete boundary of the trabecular bone image 430 can be defined, and the entire trabecular bone image 430 can be included in the attenuation average. Optionally, the portion of the trabecular bone image 430 comprising the basivertebral vein image 700 is not included in the region of interest boundary, as illustrated by a complex shaped region of interest 820 in FIG. 20.

FIGS. 21-25 illustrate further embodiments of the present invention that provide fully automated methods of locating a region of interest in the vertebral bone of a patient after the reference sample images 444, 448, 452, 456, 460, are located, and after the scale factor for the image is calculated, as discussed above. Rather than having the operator position the region of interest in the trabecular bone image 430, as illustrated in FIG. 16, or having the operator position a large region of interest to encompass a portion of the trabecular bone image 430, as illustrated in FIG. 17, in the embodiment of FIGS. 21-24, algorithms are provided that search for the trabecular bone image 430 by starting at one of the reference sample images (e.g., preferably the third reference sample image 452) and then searching upward in the image (i.e., in the Y-direction) until the trabecular bone image 430 is found.

Figure 21:
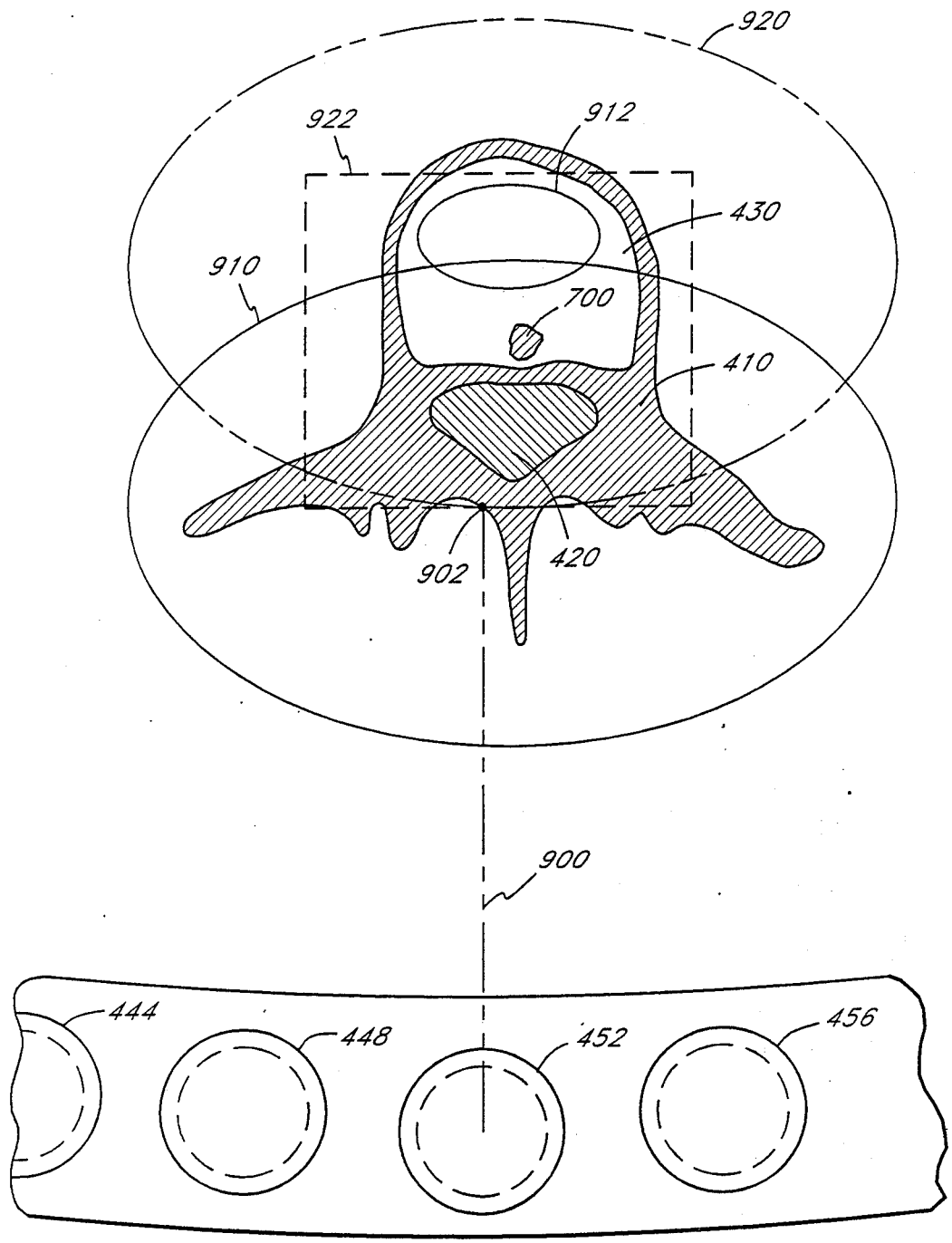
FIG. 21 illustrates a search algorithm that searches vertically upward from the third reference sample image to find the cortical bone of the vertebral body and automatically positions a search region of interest that encompasses a portion of the trabecular bone of the vertebral body.
Figure 22:
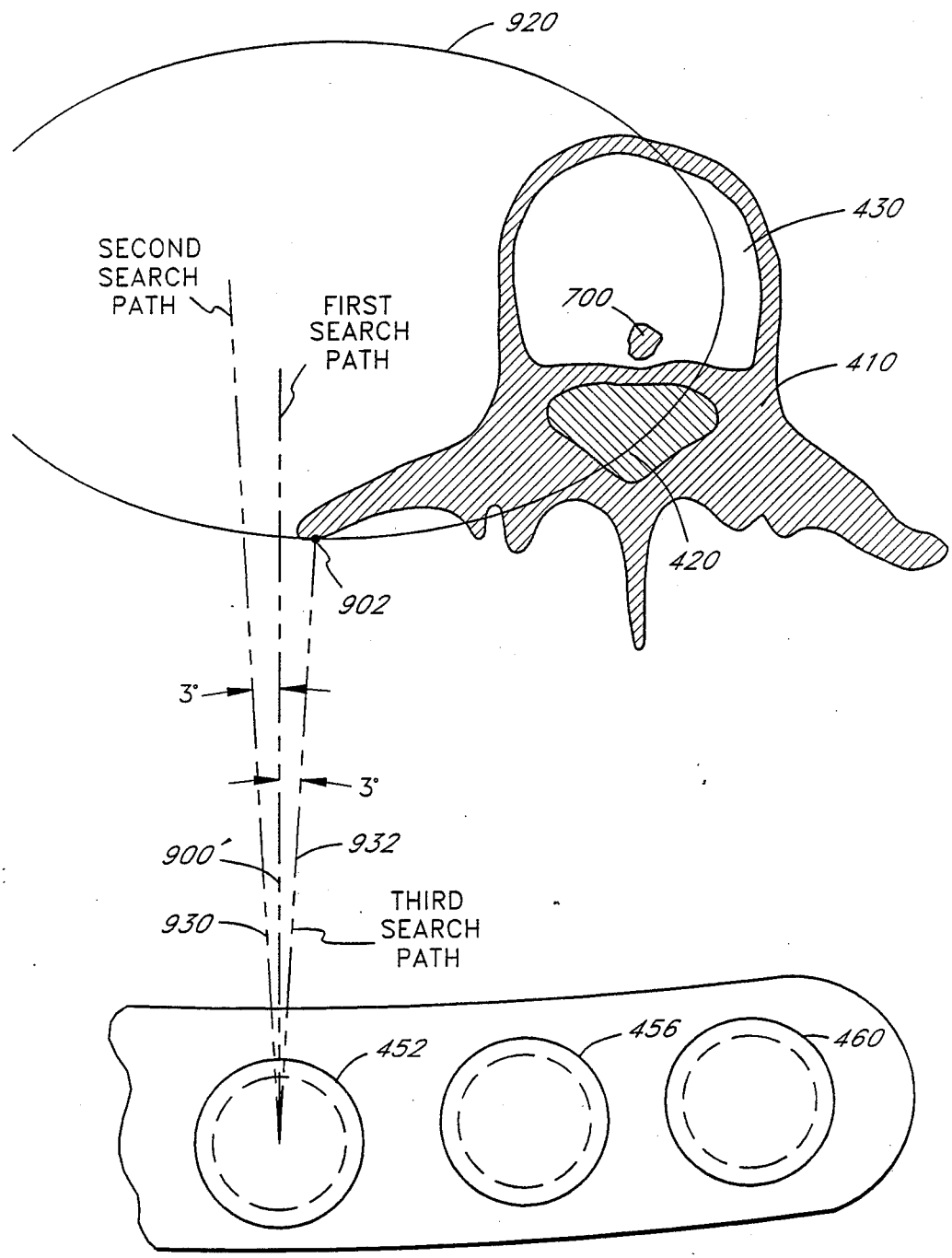
FIG. 22 further illustrates the alternative search paths taken by the search algorithm of FIG. 21 when the cortical bone is not found on the original search path.
Figure 23:
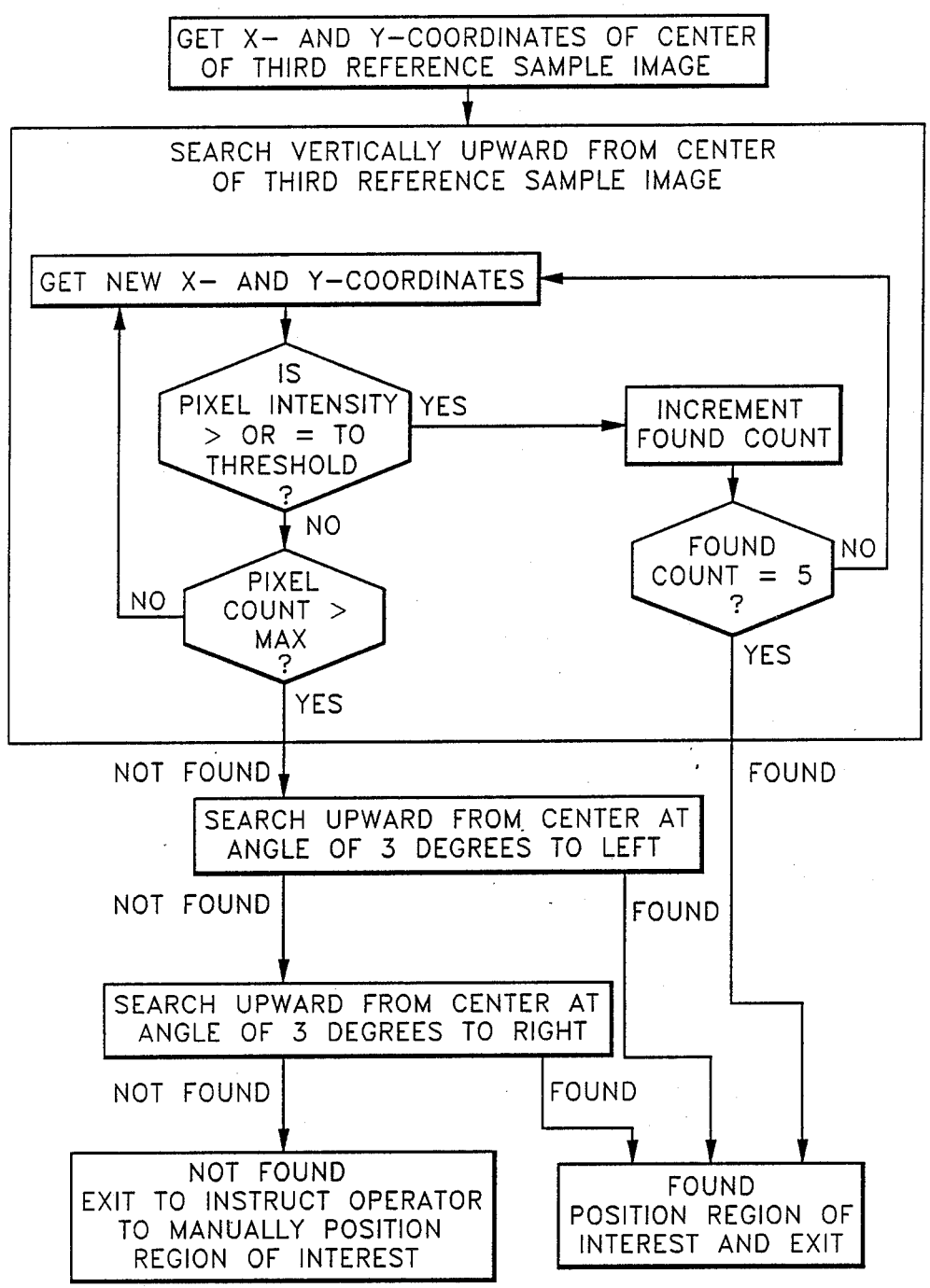
FIG. 23 is an exemplary flow chart for the search algorithm of FIGS. 21 and 22.

FIGS. 21-23 illustrate a first embodiment for automatically finding the trabecular bone image 430. In FIG. 21, the search algorithm starts at the X- and Y-coordinates of the center of the third reference sample image 452. Then, while maintaining the X-coordinate constant, the algorithm sequentially decreases the Y-coordinate (i.e., moves upward on the image as illustrated by a search path 900 represented by a phantom line) and compares the pixel intensities of the image at each new Y-coordinate with a threshold pixel intensity that is selected to be equal to or greater than the expected pixel intensities for trabecular bone image 430. For example, the threshold pixel intensity can be advantageously selected to be approximately the same as the pixel intensity of the third reference sample image 452.

Figure 20:
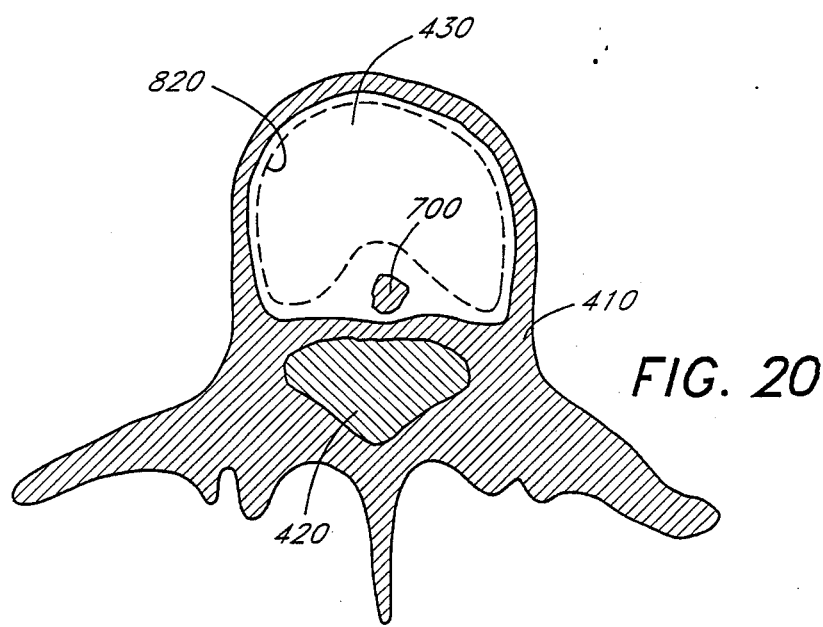
FIG. 20 is view similar to FIG. 16 illustrating a region of interest that includes a large portion of the trabecular bone image but does not include the basivertebral vein area of the image.

When a first pixel 902, having an intensity equal to or exceeding the threshold intensity is found, it is likely that the pixel 902 at the current X- and Y-coordinates corresponds to a portion of the cortical bone image 410; however, since there can be anomalies in the image that are not part of the vertebral body image, the algorithm advantageously continues searching in the same vertical direction (i.e., along the path 900) until a predetermined number (e.g., 5) pixels are found that have intensities equal to or greater than the threshold. When the predetermined number of pixels are found, the algorithm then establishes a search region of interest (ROI) 910 using the first pixel 902 as a starting location. For example, the search ROI 910 can be an elliptical search ROI such as was described above with respect to FIG. 17. The dimensions of the search ROI 910 are advantageously selected to be sufficiently large enough to encompass the trabecular bone portion 430 of the vertebral body image. Thereafter, the algorithm proceeds to position a region of interest 912 within the trabecular bone image 430. For example, the region of interest 912 can be elliptical as described above with respect to FIGS. 17 and 18. The algorithm can advantageously provide a complex region of interest such as illustrated in FIGS. 19 and 20.

Since it is likely that the first pixel 902 will comprise a portion of the cortical bone image 410 proximate to the lower portion of the image of the vertebral body, an alternative search ROI 920 can be advantageously positioned as illustrated by a phantom outline in FIG. 21. Rather than centering the alternative search ROI 920 on the first pixel 902, the first pixel 902 is included as part of the lower boundary of the alternative search ROI 920. The alternative search ROI 920 can be elliptical in shape, as illustrated in the phantom outline, or an alternative shape, such as a rectangle, as illustrated by the alternative search ROI 922 in dashed lines.

Referring now to FIG. 22, if the search algorithm does not find a predetermined number of pixels having the requisite intensity within a predetermined number of pixels after beginning the search along a first search path 900' (e.g., 200 pixels above the third reference sample image 452), the search algorithm reinitiates the search along a second search path 930 (also in phantom lines) that is offset to the left, for example, from the first search path 900' by a predetermined angle (e.g., 3 degrees). This may occur, for example, when the operator does not have the patient positioned properly with respect to the calibration phantom. The algorithm then proceeds along the second search path 930 using the same criteria for selecting a first pixel and a predetermined number of additional pixels to indicate that the cortical bone image 410 is found. If, as illustrated in FIG. 22, the second search path 930 does not intersect the cortical bone image 410 within a predetermined number of pixels from the starting location, then a third search path 932 is defined at a second predetermined angle (e.g., 3 degrees) in the opposite direction from the first search path 900' (e.g., to the right in this example). Again, the algorithm proceeds along the third search path 930 until the predetermined number of pixels are found that meet the search criteria or until the number of pixels searched exceed the predetermined number of search pixels. As illustrated in FIG. 22, the first pixel 902 is found along the third search path 930. For an image where the third search path 930 does not intersect the cortical bone image 410 or the trabecular bone image 430, additional search paths can be sequentially defined at increasing angles from the first search path, or, in the alternative, the algorithm can exit and return control to the operator for manual placement of the search ROI 910. This may occur, for example, when the patient has severe osteoporosis wherein the mineral content of the bone is sufficiently low that little, if any, of the image of the cortical bone or trabecular bone has intensities above the threshold.

The search methods of FIGS. 21 and 22 can also be understood by referring to FIG. 23 which is an exemplary flow chart of the described algorithm. It should be understood that the activity blocks captioned "SEARCH UPWARD FROM CENTER AT ANGLE OF 3 DEGREES TO LEFT" and "SEARCH UPWARD FROM CENTER AT ANGLE OF 3 DEGREES TO RIGHT" are substantially identical to the activity block captioned "SEARCH VERTICALLY UPWARD FROM CENTER OF THIRD REFERENCE SAMPLE IMAGE" and include the same activity and decision blocks; however, the new X- and Y-coordinates are obtained by modifying both the X- and Y-coordinates in accordance with the selected angle.

Figure 24:
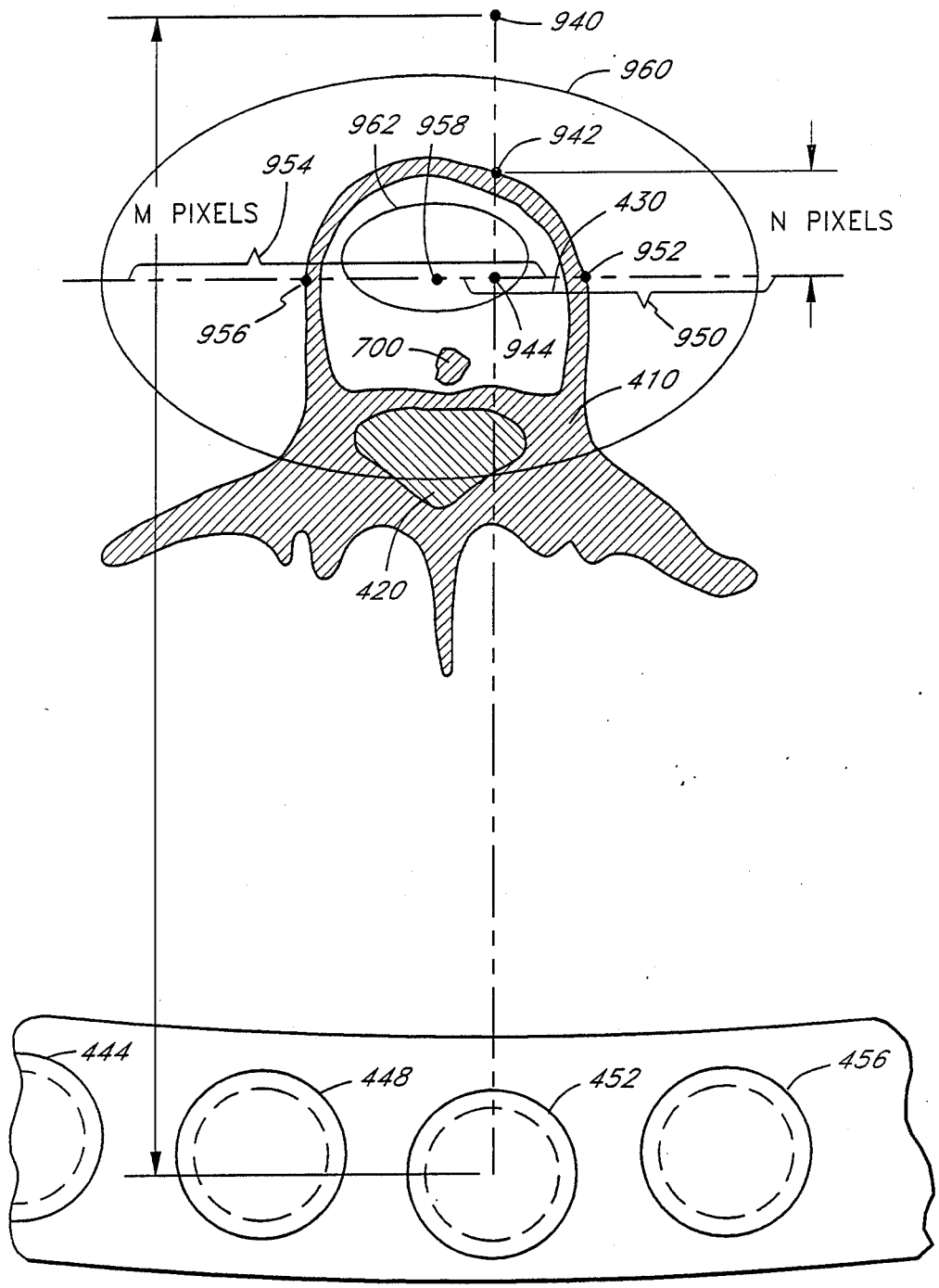
FIG. 24 illustrates an alternative search for finding the trabecular bone in the vertebral body.
Figure 25:
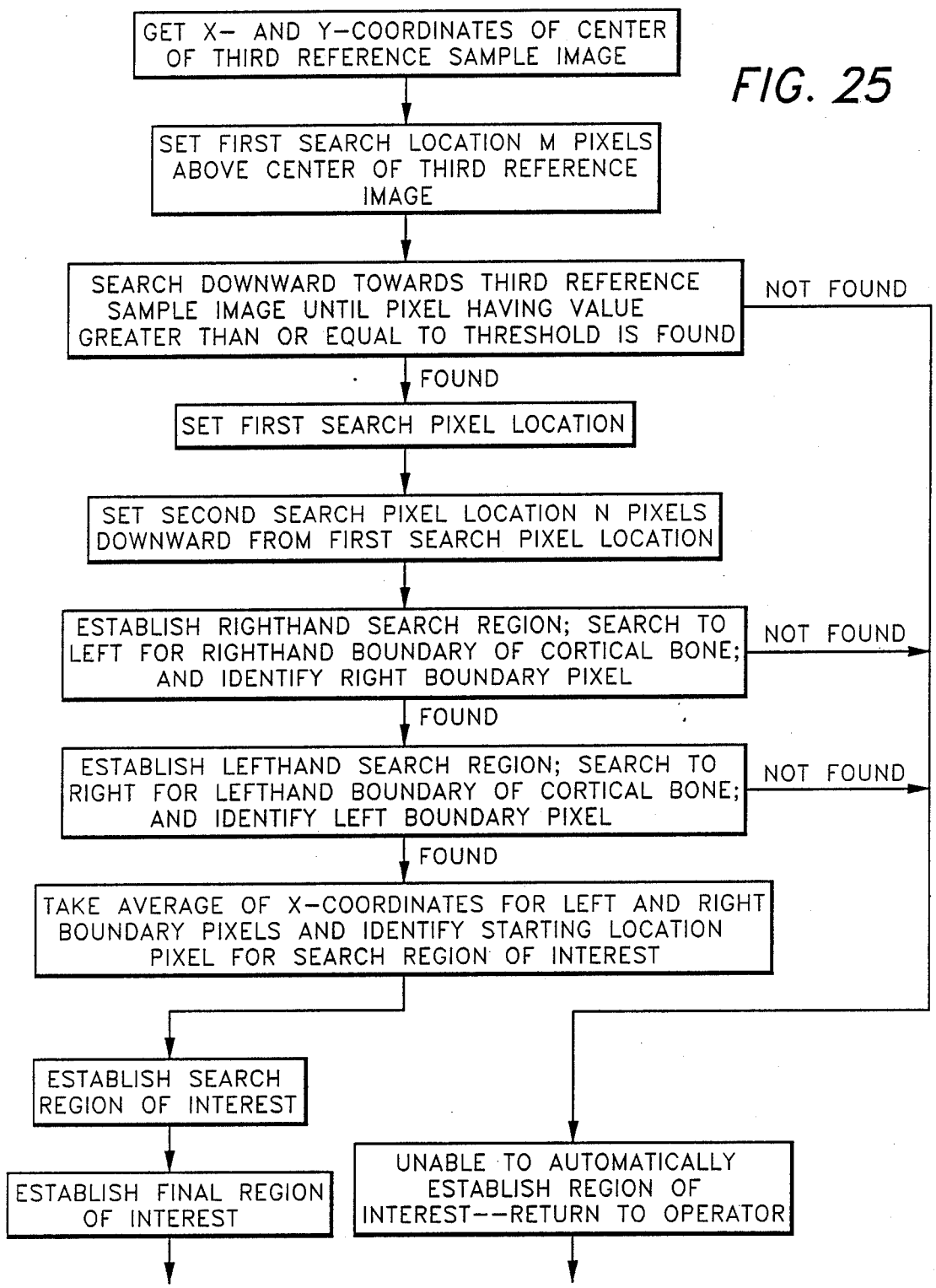
FIG. 25 is an exemplary flow chart for the search algorithm of FIG. 24.

When an image of the vertebral body of a patient is properly done, it can be assumed that the vertebral body will be located approximately above the third reference sample 152 of the phantom 140 and that the vertebral body will be located within a range of distances from the third reference sample 152. FIGS. 24 and 25 illustrate an alternative search algorithm based upon these assumptions. As illustrated in FIG. 24, the algorithm first positions a first search location 940 that has X- and Y-coordinates corresponding to a predetermined number M of pixels directly above the third reference sample image 452. The predetermined number M of pixels is selected such that the first search location is above the expected top of the image of the vertebral body, as illustrated in FIG. 24. For example, the Y-coordinate of the first search location 940 is advantageously selected such that the predetermined number M of pixel above the third reference sample image 452 corresponds to a physical distance of approximately 80 millimeters above the third reference sample 152. The Y-coordinate of the first search location 940 will thus depend upon the scale of the image. In one exemplary embodiment, each pixel corresponds to approximately 0.6 millimeters so that the first search location 940 is positioned 130 pixels above the third reference sample image 452. The algorithm begins searching vertically downward from the first search location 940 and locates a first search pixel 942 that has an intensity having a magnitude greater than or equal to a predetermined threshold magnitude that is selected to correspond to the expected magnitude of the cortical bone image 410. After finding the first search pixel 942, the algorithm defines a second search pixel 944 that has a Y-coordinate a second predetermined number N of pixels below the first search pixel 942 so that the second search pixel 944 should be at a vertical distance well within the vertical range of the trabecular bone image 430.

After locating the second search pixel 944, the algorithm illustrated in FIG. 24 searches for the left and right boundaries of the cortical bone image 410. First, the algorithm defines a righthand search region 950 that begins a first predetermined number of pixels to the right of the second search pixel 944 a second predetermined number of pixels to the left of the second search pixel 944. The algorithm then starts searching at the rightmost edge of the righthand search region 950 and moves horizontally to the left until it finds the right boundary of the cortical bone image 410 (i.e., it finds a pixel having an intensity magnitude greater than or equal to the expected magnitude of a pixel in the cortical bone image 410). It defines a right boundary pixel 952 at the right boundary of the cortical bone. Thereafter, the algorithm defines a lefthand search region 954 that begins the first predetermined number of pixels to left of the second search pixel 944 and ends the second predetermined number of pixels to the right of the second search pixel 944. The algorithm begins searching at the leftmost edge of the lefthand search region and moves horizontally to the right until it finds the left boundary of the cortical bone image 410. It defines a left boundary pixel 956 at the left boundary of the cortical bone image 410. The algorithm then finds the center of the trabecular bone image 430 along the horizontal line between the right boundary pixel 952 and the left boundary pixel 956 by averaging the X-coordinates of the two pixels. It then defines a starting location pixel 958 for a search ROI 960, which may be elliptical in shape such as the elliptical search ROI 720 described above in connection with FIG. 17. Thereafter, the algorithm generates a new region of interest 962 in accordance with one of the methods describe above with respect to FIGS. 17-20.

For some patients having poorly defined images, such as may be caused by advanced osteoporosis, the algorithm may not find the right boundary pixel 952 or the left boundary pixel 956. In that event, the algorithm returns control to the operator so that the operator can position the search ROI, as illustrated above. It should be understood that for the majority of patients, either of the above described automatic techniques provides a fast and efficient method for placing a region of interest within the trabecular bone image 430 of the vertebral body.

FIG. 25 is an exemplary flow chart of the algorithm described above with respect to FIG. 24. The activity blocks and decision blocks correspond to the foregoing description.

Attached hereto as a microfiche appendix is a software listing of the source code for an exemplary program that implements the above-described aspects of the invention. The source code is written in FORTRAN IV.

The foregoing aspects of the invention are significant improvements over the manually-assisted procedures heretofore used because the operator is not provided with an opportunity to introduce a human error into the procedure. Furthermore, the centers of the reference sample images are determined with significantly greater reproducibility so that the probability of defining a region of interest that encompasses pixels outside a reference sample image is substantially reduced or eliminated.

One skilled in the art will understand that the abovedescribed method will work with phantom images and reference sample images having geometries other than the circular geometry presented. Furthermore, the foregoing method can be used to find the centers of all the reference sample images rather than finding two centers and calculating the coordinates of the other reference sample images.

Description of the Histogram Analysis Technique

FIGS. 26-31 illustrate an alternative method of analyzing a region of interest that has been defined on an image. The method is referred to herein as the histogram ROI analysis method and is described in connection with FIGS. 26-31. The histogram ROI method is particularly useful for analyzing tissue target regions having irregular shapes, for analyzing large numbers of nodules or masses of small size, and for analyzing nonhomogeneous tissues (i.e., tissues that include other materials or combinations of tissue components within the boundaries of the defined region of interest). This method also has advantages where precise ROI placement is difficult or tedious, or when it is desireable to quantify two or more components in the same ROI, such as contrast agents, for example, Gadolinium-DTPA in MRI, and iodine-based agents in CT and digital radiography, and to identify muscle and fat or trabecular bone and fat.

The method will first be described with respect to the analysis of the mineral content of the trabecular bone of the vertebral body. As discussed above, it is particularly advantageous to include as much of the trabecular bone image 430 in a defined region of interest so that the average attenuation is accurately calculated and thus the average density is also accurately calculated. Thus, the preferred embodiments of the present invention define large regions of interest that are within the boundaries of the trabecular bone image 430 and that preferably conform to the boundaries of the trabecular bone image 430. For example, FIGS. 19 and 20 illustrate two such irregularly-shaped regions of interest. FIG. 20, in particular, includes a curve in the lower boundary of the region of interest 800 that bypasses excludes the basivertebral vein image 700 from the region of interest 800.

Figure 26:
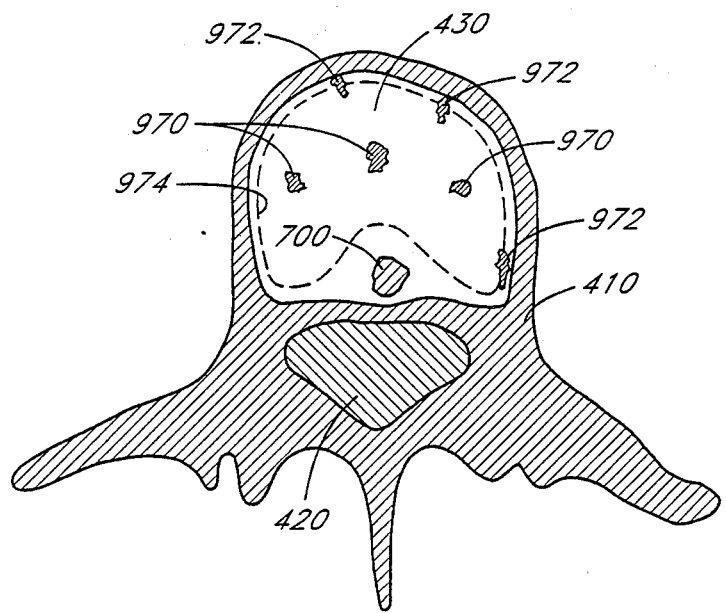
FIG. 26 illustrates an exemplary vertebral body image having inhomogeneities in the trabecular bone image and further illustrating a region of interest that includes the inhomogeneities within its boundaries.

Although the irregularly-shaped regions of interest provide substantial improvement over the smaller elliptical regions of interest, in some cases where there are significant irregularities in the tissue to be analyzed, it is not practical to define the region of interest to exclude these irregularities. For example, as illustrated in FIG. 26, the trabecular bone image 430 may include a plurality of areas 970 of increased bone density caused by calcium deposits, or the like, or there may be plural fragments 972 of the higher density cortical bone image 410 protruding into the trabecular bone image 430. Although the number of the irregularities may be relatively few, these higher density portions of the cortical bone fragments 972 and mineral deposits are included in the calculated average of the density of the trabecular bone image 430 and thus cause the calculated bone mineral density to be greater than otherwise. The method described hereinafter provides a significant improvement in the calculated density without requiring the use of a smaller region of interest and without requiring the definition of an complex region of interest to eliminate the irregularities. The method is particularly advantageous when combined with the abovedescribed, fully automated placement of the region of interest, since little or no operator intervention is required to compensate for the inhomogeneities. Thus, as illustrated in FIG. 26, a region of interest 974 can be defined that includes some of the inhomogeneities 970, 972 within its boundaries.

Figure 27:
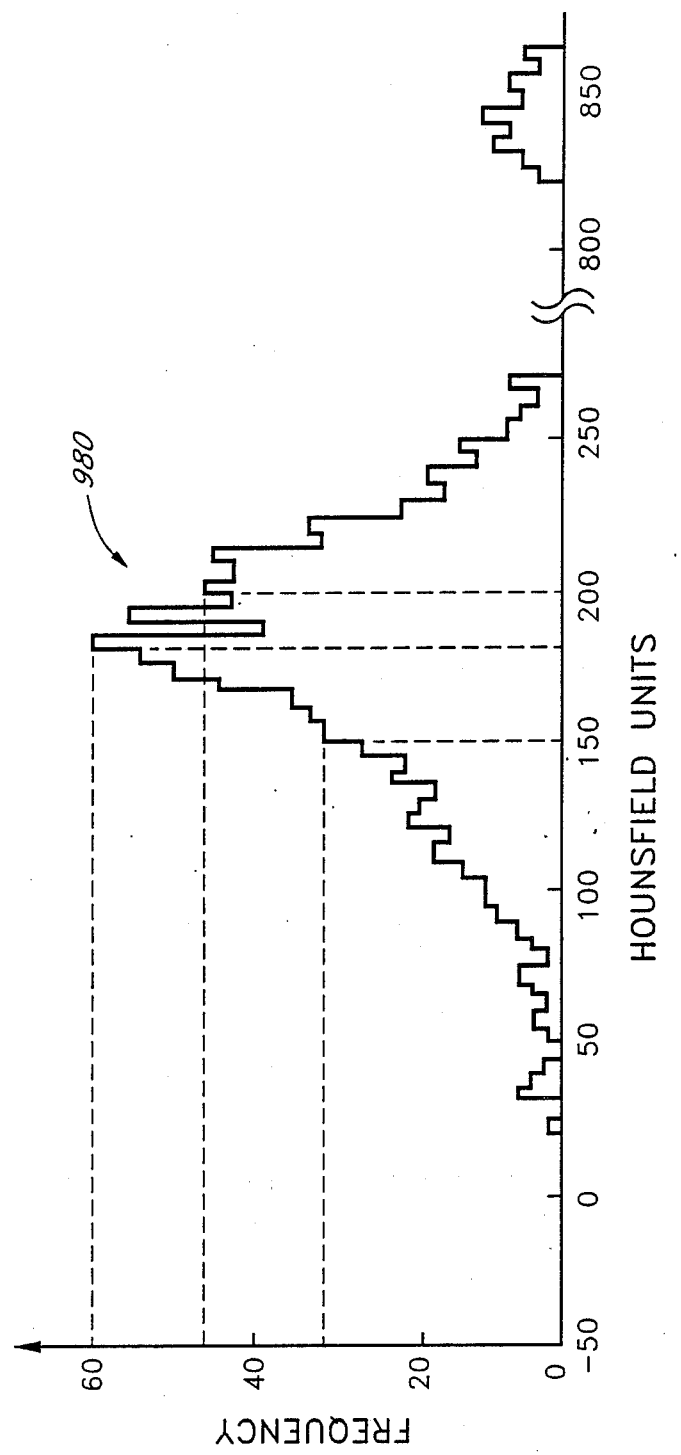
FIG. 27 is a plot of a histogram of the pixels in the region of interest of FIG. 26, wherein the frequencies of occurrence of image pixels corresponding to particular Hounsfield units are plotted versus the Hounsfield units.

FIG. 27 illustrates a histogram 980 of the calculated densities of the tissues corresponding to the portion of the trabecular bone image within the region of interest 974. The histogram 980 is a plot of the Hounsfield units along the horizontal axis of a graph with the number of pixels within the defined region of interest 974 (FIG. 26) having measured Hounsfield units (i.e., attenuations) plotted on the vertical axis. The vertical axis is labelled "FREQUENCY" to represent the frequency of occurrence of pixels having a particular measured Hounsfield unit magnitude. For example, the Hounsfield unit 200 is illustrated as having a frequency of 44. This means that 44 of the pixels within the region of interest 974 were measured and calculated to have an attenuation value of 200 Hounsfield units. Similarly, the Hounsfield unit 150 is illustrated as having a frequency of 30, indicating that 30 of the pixels within the region of interest 974 have an attenuation value of 150 Hounsfield units. It can be seen that the plot of the frequency of occurrences has an approximately Gaussian distribution around the peak frequency of occurrence at approximately 180 Hounsfield units.

The average attenuation represented by the pixels within the region of interest is obtained by multiplying each measured Hounsfield unit by the frequency of that Hounsfield unit; summing the products; and dividing by the total number of pixels included in the calculation. In other words:

$$HU_{AVG} = (\Sigma HU_i n_i)/\Sigma n_i, \ i = 1 \ldots m \quad (3)$$

where $HU_{AVG}$ is the calculated average attenuation in Hounsfield units; $HU_i$ is a particular Hounsfield unit; $n_i$ is the number of occurrences (i.e., frequency) of the Hounsfield unit $HU_i$; and m is the total number of different Hounsfield units considered in the calculation.

As set forth above, the expected range of attenuations of the trabecular bone image 430 is approximately 40–300 Hounsfield units, whereas the mineral deposits 970 and the cortical bone fragments 972 are likely to have attenuations in the range of 500–1000 Hounsfield units. As illustrated, the histogram 980 includes a significant concentration of pixels in the range of 150 to 225 Hounsfield units with a peak frequency of approximately 60 at approximately 180 Hounsfield units. The histogram 980 further includes a smaller frequency peak at approximately 850 Hounsfield units. However, the frequency at the smaller peak is 10, which is substantially smaller than the peak at 180 Hounsfield units. Thus, it can be concluded that the pixels in the range around 850 Hounsfield units are inhomogeneities of higher density and may be advantageously excluded from the calculation of the average intensity (i.e., density) of the pixels within the defined region of interest. The present invention eliminates the inhomogeneities from the calculations by assuming that the peaks in the frequencies of the pixel intensities and the surrounding pixel intensities are representative of the average intensities of pixels corresponding to the trabecular bone image 430. For example, in one exemplary embodiment of the present invention, the average intensity of the trabecular bone image 430 is calculated by including only those pixels having a frequency of occurrence within 50 percent of the Gaussian histogram peak. In FIG. 27, the peak frequency of occurrence is 60. Thus, only those pixels having Hounsfield unit measurements having a frequency greater than or equal to 30 are included in the calculation. Other criteria could be used, such as 40 percent, or the like; however, 50 percent has been found to be an acceptable criteria with respect to the trabecular bone analysis. By using this criteria, the secondary peak and the surrounding occurrences in the 850 Hounsfield unit range are not included in the calculations and thus do not cause the calculated average intensity (i.e., density) to be biased towards a higher number. Although a number of pixels having measured Hounsfield units in the expected range for the trabecular bone are excluded from the measurement, it can be seen that the lower frequency Hounsfield units above and below the peak are distributed approximately symmetrically about the peak and thus would not have a substantial affect on the calculated average. A perfectly homogeneous attenuating region of one material would be expected to produce a symmetrical Gaussian distribution which is well defined. The conventional region of interest averaging procedure and the histogram analysis method described herein would be expected to provide equivalent results for such a well defined Gaussian distribution.

In contrast to the distribution of occurrences around the peak of the plot which may have a small effect on the calculated average, the small number of occurrences in the 850 Hounsfield unit range would bias the average in one direction, particularly since, as can be seen from Equation (3) above, each occurrence of a pixel having a Hounsfield unit in the 850 Hounsfield unit range has a more significant effect on the calculated average than each occurrence of a Hounsfield unit nearer to the peak in the histogram.

The histogram calculations are performed automatically. After the region of interest 974 is defined by positioning an elliptical search ROI or other ROI, as discussed above, an algorithm systematically evaluates each pixel within the defined region of interest. As each pixel is evaluated, a running total for each of the calculated Hounsfield units is maintained. For example, in an exemplary implementation, a cell in a memory array 1000 is provided for each of the Hounsfield units in the expected range of Hounsfield units. The memory array 1000 is illustrated in FIG. 28. Each time a pixel is evaluated, the counter in the memory array 1000 corresponding to the calculated Hounsfield unit is incremented. After the entire region of interest has been evaluated, the memory array 1000 corresponds to the histogram 980 of FIG. 27. The counters in the memory array 1000 are then scanned to find the peak number of occurrences, for example, by sorting the array in order of frequency of occurrence of each Hounsfield unit to provide a sorted table 1010 or histogram plot in FIG. 29. For example presented above, the counter for the Hounsfield unit 180 will have a total count of 60 and is shown at the top of the table 1010.

Thereafter, the histogram average of the Hounsfield units is calculated in accordance with Equation (3) above by multiplying each Hounsfield unit by its corresponding frequency of occurrence and summing the products for each Hounsfield unit having a frequency of occurrence greater than or equal to a predetermined percentage of the peak frequency of occurrence (e.g., 50 percent). In this example, each of the Hounsfield units having a frequency of occurrence greater than or equal to 30 is included in the sum of the products. The sum of the products is then divided by the sum of the occurrences of the Hounsfield units included within the sum of the products to obtain the average value of the Hounsfield units representing the trabecular bone image 430. As set forth above, the inhomogeneities (i.e., irregularities) in the trabecular bone image 430 are automatically removed from the calculation because the frequencies of occurrence are less than the selected cutoff frequency of one-half the peak frequency, thus providing the ability to discriminate pixels on the basis of the Hounsfield unit value as well as their location within the region of interest.

Another aspect of the present invention is to use the above-described histogram technique to evaluate irregularly-shaped images of soft tissue regions or masses such as are obtained by CT or magnetic resonance imaging (MRI) of a patient's lung or brain. As is well-known in the medical field the character of a tumor can be evaluated in part by determining the physical density of the tumor. See, for example, S. S. Siegleman, et al., "CT of the Solitary Pulmonary Nodule," *AMERICAN JOURNAL OF ROENTGENOLOGY*, Vol. 135, 1980, pp. 1-13. For example, it is known that a benign tumor typically has a higher density than a malignant tumor. Thus, by evaluating the tissue density as described herein, the two types of tumors may be able to be differentiated without the need for a high risk biopsy of an organ such as the lung. Furthermore, by applying the histogram technique to a first tumor and determining the average density of the tumorous tissues, other tumors having similar densities can be readily located in the image. The coordinates of the tumors can be saved and compared with images of the same patient taken at different times to determine whether the tumors are increasing or decreasing in size following therapy and whether additional tumors are appearing.

Figure 30:
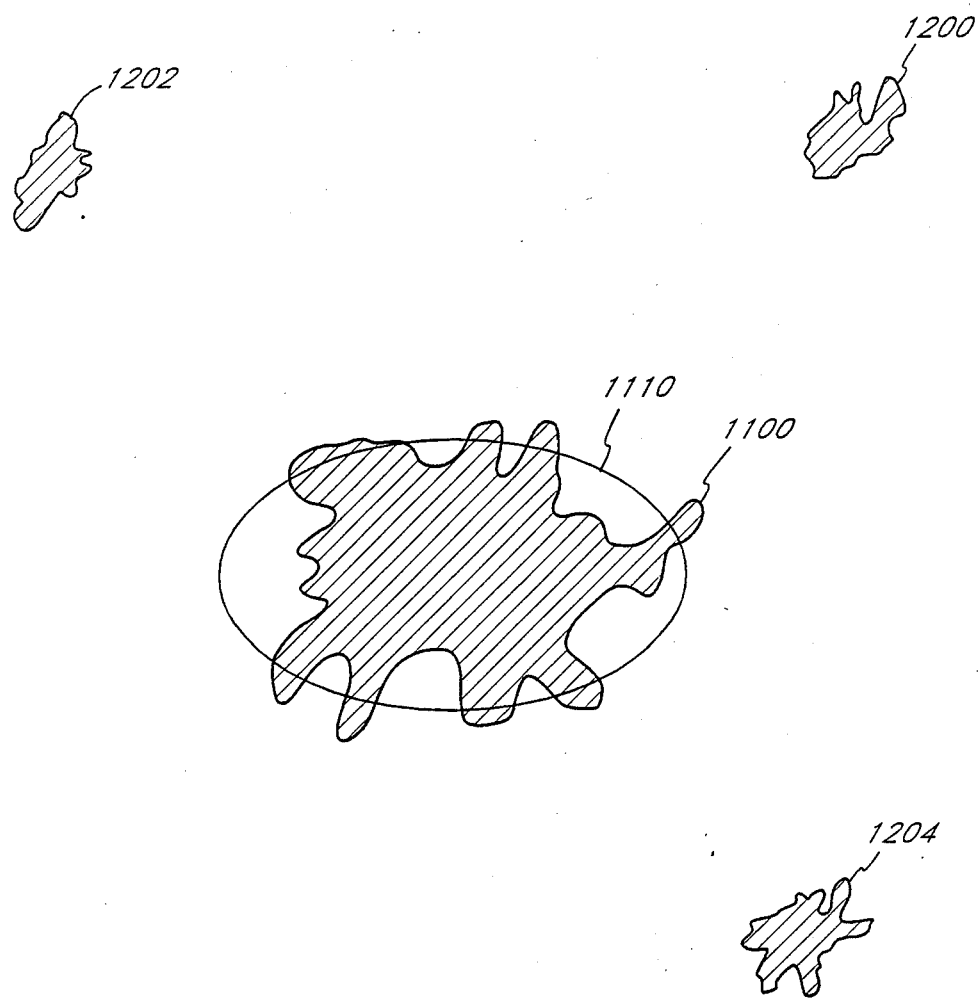
FIG. 30 illustrates an exemplary portion of an image of a patient's lung and shows images of tumorous tissues in the lung image, wherein one of the tumorous tissue images has a region of interest positioned around it.
Figure 31:
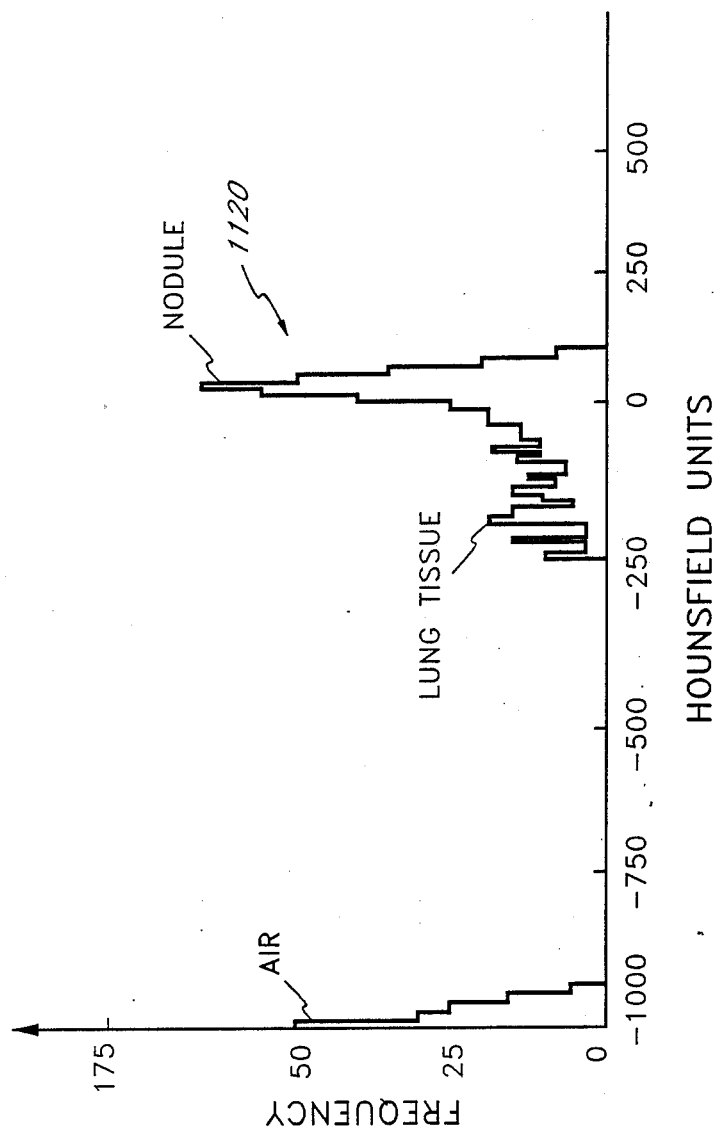
FIG. 31 is a histogram plot of the frequencies of occurrence of the Hounsfield units within the region of interest in FIG. 30, showing the peaks corresponding to air, the lung tissue and the tumor tissue.

FIG. 30 illustrates an exemplary image 1100 of an irregular-shaped tumor in the image of a patient's lung. As can be seen, the irregular shape of the tumor image 1100 makes it impractical to identify the boundaries of the tumor image so that its size, mass and density can be calculated; however, there have been attempts to do so with varying degrees of success. Notwithstanding the success of these attempts, it should be apparent that the manual effort or computational steps required to create a region of interest within the boundaries of the tumor image 1100 or to determine its boundaries are quite extensive.

This aspect of the present invention takes advantage of the histogram technique, described above, and starts with a region of interest 1110 that is only approximately positioned around the tumor image 1100 such that all, and perhaps a substantial portion of surrounding tissue as well as the tumor image 1100 are enclosed within the boundaries of the region of interest 1110. The key advantage is that the precise placement of the region of interest 1110 is not required to differentiate the tumor tissue and to allow accurate measurements of its size and density. After the region of interest 1110 is positioned, the steps described above for the histogram analysis are performed for the pixels within the region of interest 1110 to generate a histogram 1120 illustrated in FIG. 31. Since the pixels surrounding the tumor image 1100 represent air or lung tissues having a high water content, the histogram of FIG. 31 has distinct peaks corresponding to air (Hounsfield units in the range of −1000) and soft tissue (Hounsfield units in the range of −250 to 0). The histogram of FIG. 31 also has a peak in a higher range of Hounsfield units corresponding to the tumorous tissue which can be identified. The peak in the high negative range is automatically eliminated since it clearly is caused by the air in the lung. The peak in the range of −250 to 0 Hounsfield units is sufficiently smaller than the peak in the higher range of Hounsfield units so that it is eliminated as described above. Thus, only those pixels corresponding to the tumor image 1100 are included in the calculation of the average density or size. Therefore, the histogram provides an accurate calculation of the density of the tissue within the irregularly-shaped tumor without requiring laborious manual placement of a corresponding irregularly-shaped region of interest or complex computations to provide computer generated boundaries or regions of interest.

After calculating the average pixel intensity of the tumor image 1100, the calculated average pixel intensity can be advantageously compared to other pixel intensities in the lung image to find other portions of the lung image having the same or similar pixel intensities, for example, the portions 1200, 1202, 1204. When the portions 1200, 1202, 1204 are located, the pixels having the requisite range of intensities can be highlighted on the displayed image so that other tumors of similar densities can be readily spotted by the operator for viewing and so that the tumors will be automatically highlighted to facilitate the transfer of the image to photographic film for permanent records. This highlighting (by selecting a level of Hounsfield units and a window about that level) can be readily accomplished by selecting a range of pixel intensities that are to be displayed in a manner well-known to the art. For example, if the tumor image 1100 has an average pixel intensity of 100 Hounsfield units, then it and the other tumors can be optimally viewed and filmed by automatically displaying those pixels having intensities in the range of 90 to 110 Hounsfield units with preferred contrast and brightness.

In addition to the display feature described above, the coordinates of the original tumor image 1100 and the additional tumor images 1200, 1202, 1204 can be stored on a permanent record for the patient. When the patient's lungs are imaged at a later time, the most recent image can be highlighted as described above and visually compared to the previous image to determine whether additional tumors have appeared and whether the tumors have changed in size. Furthermore, although the coordinates will likely differ due different placement of the patient within the imaging field, the coordinates of the various tumors found in the most recent image can be correlated with the coordinates of previous images by overlay techniques.

Exemplary Applications of the Present Invention

Discrimination of tissue components and quantification of properties of these components, such as density and mass, have several important medical applications. Heretofore, regions of interest placed manually and boundary detection techniques have typically been used with varied success. The techniques described herein utilize a phantom or reference samples to more accurately quantify the measured values on an absolute scale of reference, as well as automating the placement of regions of interest in the reference sample and in regions of tissue within the patient image. Furthermore, a significant advance of the method of the invention is the ability to discriminate tissue components by histogram analysis in combination with automated phantom calibration.

In some cases, tissue components may be separated physically in space, such is the case with the cortical bone surrounding the trabecular bone of the vertebral body. In such cases, regions of interest can be used to differentiate the two tissues by including only the trabecular bone within the region of interest.

In other cases, the tissue region to be analyzed may contain multiple components which are homogeneously distributed. For example, combinations of muscle and fat, trabecular bone and fat, trabecular bone and cortical bone fragments or hard, high density deposits, or contrast agents in organs; all of which may make it impossible to spatially isolate the components in a region of interest. The above-described histogram analysis method provides an accurate technique for identifying the tissue components and quantifying their physical properties by cross-referencing the measured properties with the measured properties of the reference phantom that is imaged simultaneously with the patient. By combining the automated region of interest positioning methods with the histogram analysis method, the tissue analysis can be accomplished automatically, thereby improving the speed and accuracy of the procedure.

An additional aspect of the present invention is the ability to quantify regions or tissue targets that may be too small, too irregular and/or too numerous to analyze by conventional region of interest or boundary detection methods. The histogram analysis in combination with the simultaneous imaging of the calibration phantom method allows a relatively imprecise region of interest to be positioned on the target tissue region while providing accurate results. The target tissue region is then analyzed and identified. Other tissue regions having similar properties can then be identified. This method is advantageously used, for example, to locate nodules in the lungs for differentiation of malignant from non-malignant tumors.

The histogram analysis method can also be used to quantify two or more tissue components in a region of interest. For example, the method can be used to quantify both the cortical bone and trabecular bone in the hip or femur of a patient. In such cases, the histogram will include two distinct peaks which can each be analyzed to determine the average density separately of each component.

Although the preferred embodiments of the present invention have been described and illustrated, it will be apparent to those skilled in the art that various changes and modifications can be made to the present invention without departing from its spirit. Accordingly, the scope of the present invention is deemed to be limited only by the scope of the following appended claims.

What is claimed is:

1. A method for analyzing a cross-sectional digitized image of the internal structure of a body having digitized image pixels with intensities that vary in accordance with the physical characteristics of the body, said digitized image being provided by a medical imaging system, so as to measure the physical characteristics of a particular portion of the body structure, comprising the steps of:

(a) positioning a calibration phantom proximate to the body so that a representation of a cross-section of said calibration phantom is included as part of said digitized image, said calibration phantom having at least first and second calibration portions, each having known, calibrated physical characteristics, said digitized image further including first and second calibration portion images, each having a respective intensity corresponding to the physical characteristics of said first and second calibration portions, respectively;

(b) automatically comparing the intensities of the digitized image pixels on a first axis with a predetermined range of intensities corresponding to the intensity of said first calibration portion image to locate image pixels having intensities within said predetermined range of intensities;

(c) automatically geometrically locating a first center pixel on said first axis;
(d) automatically comparing the intensities of the digitized image pixels on a second axis with a predetermined range of intensities corresponding to the intensity of said first calibration portion image to locate image pixels having intensities within said predetermined range of intensities;
(e) automatically geometrically locating a second center pixel of said second axis;
(f) repeating steps (b)–(e) a selected number of times using said first and second axes so as to automatically locate the center of said first calibration portion image;
(g) automatically defining a region of interest centered on said center of said first calibration portion image upon location of said center of said first calibration image;
(h) calculating an intensity representative of the pixels within the region of interest of said first calibration portion image;
(i) repeating steps (b)–(h) for said second calibration portion image to automatically locate the center of said second calibration image, to automatically define a region of interest centered on said center of said second calibration portion image, and to calculate an intensity representative of the pixels within the region of interest of said second calibration portion image;
(j) calculating a calibration factor that relates the intensity of the pixels representative of said first and second calibration portion images with the known, calibrated physical characteristics of said first and second calibration portions of said calibration phantom;
(k) calculating an intensity representative of an image of a portion of said body structure; and
(l) applying said calibration factor to said calculated intensity of said image of said portion of said body structure to calculate the physical characteristics of said body portion.

2. The method as defined in claim 1, wherein said steps (b)–(e) are performed using the horizontal axis as the first axis and the vertical axis as the second axis.

3. A method for analyzing a cross-sectional digitized image of the internal of a body having digitized image pixels with intensities that vary in accordance with the physical characteristics of the body, said digitized image being provided by a medical imaging system, so as to measure the physical characteristics of a particular portion of the body structure, comprising the steps of:
positioning a calibration phantom proximate to the body so that a representation of a cross-section of said calibration phantom is included as part of said digitized image, said calibration phantom having at least first and second calibration portions, each having known, calibrated physical characteristics, said digitized image further including at least first and second calibration portion images, each having an intensity corresponding to the physical characteristics of said first and second calibration portions, respectively;
for each of said first and second calibration portion images, automatically comparing the intensities of the digitized image pixels with a respective predetermined range of intensities corresponding to the respective intensity of said calibration portion image to locate image pixels having intensities within said respective predetermined range of intensities, said step of automatically comparing the intensities of said digitized image pixels comprising the steps of:
finding a first digitized image pixel having an intensity within said respective predetermined range of intensities;
comparing the intensities of digitized image pixels proximate to said first digitized image pixel with said respective predetermined range of intensities;
counting the number of said proximate image pixels having intensities within said respective predetermined range of intensities; and
comparing said number of said proximate image pixels to a predetermined number and selecting one of said proximate image pixels as a starting location;
automatically locating a respective center of each of said first and second calibration portion images using said starting location selected for each of said first and second calibration portion images;
automatically defining first and second regions of interest centered on said centers of said first and second calibration portion images, respectively;
calculating intensities representative of the pixels within the regions of intensity of said first and second calibration portion images;
calculating a calibration factor that relates the intensities of the pixels representative of said first and second calibration portion images with the known, calibrated physical characteristics of said first and second calibration portions of said calibration phantom;
calculating an average intensity representative of an image of a portion of said body structure; and
applying said calibration factor to said calculated average intensity of said image of said portion of said body structure to calculate the physical characteristics of said body portion.

4. The method as defined in claim 3 wherein for each of said first and second calibration portion images, said step of automatically locating said respective center of said calibration portion image comprises the steps of:
starting with said selected proximate image pixel and comparing the intensities of image pixels in the same row on a first axis to the left and to the right of said selected proximate image pixel with said respective predetermined range of intensities and selecting the leftmost and rightmost pixels having intensities within said respective predetermined range of intensities;
selecting an image pixel substantially equidistant from said selected leftmost and said selected rightmost image pixels as a first selected center pixel;
comparing image pixels in the same column on a second axis as said first selected center pixel with said respective predetermined range of intensities and selecting the uppermost and lowermost image pixels in said column having intensities within said respective predetermined range of intensities; and
selecting an image pixel substantially equidistant from said selected uppermost and said selected lowermost image pixels as a second selected center pixel, said second selected center pixel substantially corresponding to said respective center of said calibration portion image.

5. The method as defined in claim 4, further including the steps of:

starting with said second selected center pixel and comparing the intensities of image pixels in the same row on said first axis to the left and to the right of said second selected center pixel with said predetermined range of intensities and selecting the leftmost and rightmost pixels having intensities within said predetermined range of intensities;

selecting an image pixel substantially equidistant from said selected leftmost and said selected rightmost image pixels as a third selected center pixel;

comparing image pixels in the same column on said second axis as said third selected center pixel with said predetermined range of intensities and selected the uppermost and lowermost image pixels in said column having intensities within said predetermined range of intensities; and selecting an image pixel substantially equidistant from said selected uppermost and said selected lowermost image pixels as a fourth selected center pixel, said fourth selected center pixels substantially corresponding to said center of said calibration portion image.

6. A method for analyzing a digitized image of a portion of the internal structure of a body positioned within an imaging field of an imaging system, said image having intensities that vary in accordance with the physical characteristics of the body and that vary in accordance with variations in the operational characteristics of said imaging system, said method being designed so as to measure the intensities of said digitized image and provide calibrated quantitative information regarding said physical characteristics of said body represented by said digitized image, said method comprising the steps of:

providing an object of known physical characteristics within said imaging field so that said digitized image includes at least first and second digitized representations of said known physical characteristics of said object;

locating on said digitized image first and second calibration regions positioned totally within said first and second digitized representations of said known physical characteristics of said object, said locating step for each of said first and second calibration regions comprising the steps of:

automatically comparing the intensities of discrete portions of said digitized image with a range of intensities corresponding to said known physical characteristics of said object for said calibration region; and selecting a plurality of said discrete portions having intensities within said range of intensities to comprise said calibration region;

calculating a respective intensity representative of said plurality of discrete portions of each of said first and second calibration regions;

generating a calibration factor that relates said intensities representative of said plurality of discrete portions of said first and second calibration regions to said known physical characteristics of said object; and applying said calibration factor to said measured intensities of said image to generate a quantitative representation of said image that corresponds to said physical characteristics of said image and that is substantially independent of said variations in the operational characteristics of said imaging system.

7. The method as defined in claim 6 wherein said providing step comprises the step of providing a calibration phantom filled with materials having known physical characteristics.

8. The method as defined in claim 6 wherein said comparing step comprises the step of comparing pixels in said digitized image.

9. The method as defined in claim 6 wherein said physical characteristic of said body is selected to be the magnitude of MRI signals.

10. A method for analyzing a digitized image that includes a cross-sectional digitized image of the internal structure of a body having digitized image pixels with intensities that vary in accordance with the physical characteristics of the body, said image further including a cross-sectional digitized image of a calibration phantom positioned proximate to the body, said calibration phantom having at least first and second calibration portions with known, calibrated physical characteristics and having first and second position reference portions having known physical characteristics different from said calibrated physical characteristics, said first and second position reference portions having known, fixed spatial locations with respect to said first and second calibration portions, so that said digitized image of said calibration phantom includes first and second calibration portion images having intensities corresponding to the physical characteristics of said first and second calibration portions, respectively, and so that said digitized image of said calibration phantom includes first and second position reference images of said first and second position references, respectively, said method being designed to analyze said digitized image of said calibration phantom to locate said calibration portion image, said method comprising the steps of:

defining a first area of said calibration phantom image that encompasses said first position reference image;

automatically comparing the intensities of the digitized image pixels with a predetermined threshold intensity within said first area of said calibration phantom, so as to locate a plurality of image pixels having intensities greater than said predetermined threshold intensity;

automatically locating the center of said plurality of image pixels having intensities greater than said predetermined threshold intensity; and defining said center as the first position reference center of said first position reference image;

repeating said comparing, locating and defining steps for said second position reference image to define a second position reference center of said second position reference image; and calculating the positions of said first and second calibration portion images with respect to said first portion reference center and said second position reference.

11. A method for analyzing a digitized image that includes a cross-sectional digitized image of the internal structure of a body having digitized image pixels with intensities that vary in accordance with the physical characteristics of the body, said image including a cross-sectional digitized image of the trabecular bone of a vertebra of said body surrounded by a cross-sectional digitized image of the cortical bone of said vertebra, said method designed so as to automatically locate a region of interest within an area of said digitized image that comprises said trabecular bone, said method comprising the steps of:

positioning a first region of interest in a first area of said digitized image so that said first region of interest encompasses a plurality of image pixels that includes at least part of the digitized image pixels of said trabecular bone image, said region of interest having a first center pixel located within said trabecular bone image;

comparing digitized representations of the intensities of selected image pixels within said first region of interest and selecting a threshold intensity having a predetermined magnitude less than the highest intensity of said selected pixels;

locating a first boundary pixel in a first direction from said first center pixel, said first boundary pixel having an intensity less than said threshold intensity;

locating a second boundary pixel in a second direction from said first center pixel, said second boundary pixel having an intensity less than said threshold intensity;

locating a third boundary pixel in a third direction from said center pixel; and defining a region of interest having a boundary that includes said first, second and third boundary pixels.

12. The method as defined in claim 11, wherein said digitized image pixels are arranged as a horizontal and vertical matrix of image pixels, and wherein said first direction is in a first horizontal direction from said first center pixel, said second direction is in a second horizontal direction from said first center pixel, and said third direction is along a line perpendicular to a horizontal line between said first boundary pixel and said second boundary pixel.

13. The method as defined in claim 12 wherein said cross-sectional digitized image includes an image of a calibration phantom, said image of said calibration phantom including an image of at least one reference portion of said calibration phantom, and wherein said positioning step comprises the steps of:

sequentially comparing pixels in a predetermined direction from said image of said reference portion;

locating at least one pixel having an intensity corresponding to the intensity of said image of cortical bone; and generating a region of interest proximate to said at least one pixel, said region of interest corresponding to said first region of interest.

14. A method for analyzing a cross-sectional digitized image of the internal structure of a body having digitized image pixels with intensities that vary in accordance with the physical characteristics of the body, so as to measure the physical characteristics of a particular portion of the body, comprising the steps of:

positioning a calibration phantom proximate to the body so that a representation of a cross-section of said calibration phantom is included as part of said digitized image, said calibration phantom having at least one calibration portion having known, calibrated physical and geometrical characteristics, and a reference region having preselected physical characteristics, said reference region and calibration portion being in known spatial relation, said digitized image further including at least one calibration portion image having intensities corresponding to the physical characteristics of said calibration portion and further comprising a reference region image having an intensity corresponding to the preselected physical characteristics of said reference region;

automatically scanning said reference region image to find pixels having intensities corresponding to the preselected physical characteristics of said reference region in said calibration phantom;

automatically locating the center of said reference region image upon scanning of said reference region image;

automatically geometrically determining the center of said calibration portion image using said center of said reference region, and based on said spatial relation; and automatically defining a region of interest centered on said center of said calibration portion image.

15. A method for analyzing a digitized image of the internal structure of a body having digitized image pixels with intensities having numeric values that vary in accordance with the physical characteristics of the body, said numeric values being stored in a digital storage device at storage locations corresponding to the locations of said image pixels on said image, said method being designed so as to measure the physical characteristics of a particular first region of the body structure, said method comprising the steps of:

positioning a region of interest on said digitized image, said region of interest having a boundary to encompass at least a portion of said image pixels corresponding to said first region of the body structure;

sequentially reading the stored numeric values of the intensities for the image pixels within the boundary of said region of interest and storing a count associated with each numeric value, said count for each numeric value corresponding to the number of times each numeric value occurs within said boundary, said stored counts comprising a histogram of said numeric values;

calculating a weighted average for a predetermined portion of said numeric values in said histogram, starting with the numeric value having the greatest number of occurrences, said weighted average comprising the sum of the products of each numeric value multiplied by number of occurrence, said sum of products divided by the total number of occurrences of said predetermined portion; and multiplying said weighted average by a scale factor that correlates said measured numeric values with corresponding known physical characteristics to thereby calculate the average physical characteristic of said first region of the body structure.

16. The method as defined in claim 15, further including the step of locating a second region of the body structure having physical characteristics similar to said first region of the body structure, said locating step comprising the steps of:

comparing said weighted average with the numeric values of other pixels in said image; and identifying additional image pixels in said image having numeric intensity values in a range proximate to said weighted average, said additional image pixels corresponding to said second region of the body structure.

17. A method for locating a particular portion of a body of a patient in a cross-sectional digitized image of the internal structure of said body, said digitized image having digitized image pixels with intensities that vary in accordance with the physical characteristics of the body, said method comprising the steps of:

positioning a calibration phantom proximate to the body so that a representation of a cross-section of said calibration phantom is included as part of said digitized image, said calibration phantom having at least one calibration portion having known physical characteristics;

automatically scanning said cross-sectional image in a first predetermined direction from said calibration portion so as to find a first pixel having an intensity within a predetermined range of intensities; and automatically locating a region of interest using said first pixel within an area of said digitized image that comprises said particular portion of the body.

18. The method as defined in claim 17, wherein the step of scanning said cross-sectional image is performed a predetermined number of times in said first predetermined direction so as to find a number of pixels having each an intensity within said predetermined range of intensities.

19. The method as defined in claim 17, wherein the step of locating a region of interest comprises the step of using the spatial location of said first pixel in said digitized image as a geometrical locus for said region of interest.

20. The method as defined in claim 17, wherein, in the case where no pixel is found along said first predetermined direction corresponding to said predetermined range of intensities, the step of scanning said digitized image is repeated in a second predetermined direction offset from said first predetermined direction by a predetermined angle so as to find a pixel corresponding to said predetermined range of intensities.

21. The method as defined in claim 20, wherein said scanning step is repeated along further predetermined directions until said pixel corresponding to said predetermined range of intensities is found.

22. A method for analyzing a digitized image to automatically locate a region of interest within an area of said digitized image, said digitized image including a cross-sectional digitized image of the internal structure of a body having digitized image pixels with intensities that vary in accordance with the physical characteristics of the body, said image including a cross-sectional digitized image of the trabecular bone of a vertebra of said body surrounded by a cross-sectional digitized image of the cortical bone of said vertebra, said region of interest comprising said trabecular bone, said method comprising the steps of:

automatically searching for the boundaries of said trabecular bone image by locating pixels having intensities within a range of intensities corresponding to said trabecular bone image, said searching step being performed using two directions substantially perpendicular to each other;

positioning a region of interest in an area of said digitized image, said region of interest comprising pixels, substantially all of which are within said trabecular bone image;

calculating an intensity representative of said trabecular bone image; and applying a known calibration factor is said calculated intensity of said trabecular bone image to calculate the physical characteristics of said trabecular bone.

23. The method as defined in claim 22, further including the step of positioning a search region of interest in a search area of said digitized image so that said search region of interest encompasses a plurality of image pixels, said plurality of image pixels including at least a portion of the image pixels of said trabecular bone image.

24. The method as defined in claim 22, wherein said region of interest has an elliptical shape.

25. The method as defined in claim 22, wherein said region of interest has an irregular shape, said irregular shape being selected to conform with the boundary of said trabecular bone image, said shape further selected so that the image of the basivertebral vein within said trabecular bone image is outside said region of interest.

* * * * *